United States Patent
Toner et al.

(10) Patent No.: US 8,501,213 B2
(45) Date of Patent: Aug. 6, 2013

(54) MULTIPLE DRUG DELIVERY FROM A BALLOON AND A PROSTHESIS

(75) Inventors: John L. Toner, Libertyville, IL (US); Sandra E. Burke, Libertyville, IL (US); Keith R. Cromack, Chesterfield, MO (US); Randolf von Oepen, Los Altos Hills, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/617,628

(22) Filed: Sep. 14, 2012

(65) Prior Publication Data

US 2013/0013048 A1 Jan. 10, 2013

Related U.S. Application Data

(63) Continuation of application No. 12/371,422, filed on Feb. 13, 2009, which is a continuation-in-part of application No. 11/084,172, filed on Mar. 18, 2005, now Pat. No. 8,057,813.

(60) Provisional application No. 60/554,730, filed on Mar. 19, 2004.

(51) Int. Cl.
*A61F 13/00* (2006.01)

(52) U.S. Cl.
USPC .............................. 424/422; 604/509; 427/2.1

(58) Field of Classification Search
None
See application file for complete search history.

(56) References Cited

U.S. PATENT DOCUMENTS

| | | | |
|---|---|---|---|
| 3,929,992 | A | 12/1975 | Sehgal |
| 3,993,749 | A | 11/1976 | Sehgal |
| 4,316,885 | A | 2/1982 | Rakhil |
| 4,401,653 | A | 8/1983 | Eng |
| 4,580,568 | A | 4/1986 | Gianturco |
| 4,650,803 | A | 3/1987 | Stella |
| 4,733,665 | A | 3/1988 | Palmaz |
| 4,885,171 | A | 12/1989 | Surendra |
| 4,897,268 | A | 1/1990 | Tice et al. |
| 4,916,193 | A | 4/1990 | Tang |

(Continued)

FOREIGN PATENT DOCUMENTS

| DE | 102007034991 | 1/2009 |
|---|---|---|
| EP | 0 467 606 | 1/1992 |

(Continued)

OTHER PUBLICATIONS

U.S. Appl. No. 12/371,426, Aug. 27, 2012 Supplemental Amendment and Statement of the Substance of the Interview.

(Continued)

*Primary Examiner* — Bethany Barham
(74) *Attorney, Agent, or Firm* — Baker Botts LLP

(57) ABSTRACT

Disclosed is an interventional device for delivery of therapeutic agents from an angioplasty balloon and from a prosthesis such as an intraluminal stent. The invention also relates to the method of loading the beneficial agents onto the balloon and the device, as well as the method of delivery of the agents from separate surfaces. The invention also relates to an interventional device having a prosthesis surface that is loaded with a first beneficial agent, and a balloon surface loaded with a second beneficial agent. The invention also relates to a method of loading multiple beneficial agents onto the prosthesis surfaces and the balloon surfaces, and to a method of manufacturing an interventional device for the delivery of a first beneficial agent and a second beneficial agent from separate surfaces.

14 Claims, 10 Drawing Sheets

Graph 1 Semi Quantitative Angiographic Scoring

U.S. PATENT DOCUMENTS

| | | | |
|---|---|---|---|
| 4,994,071 A | 2/1991 | MacGregor |
| 5,023,262 A | 6/1991 | Caufield |
| 5,092,877 A | 3/1992 | Pinchuk |
| 5,102,402 A | 4/1992 | Dror |
| 5,108,416 A | 4/1992 | Ryan et al. |
| 5,120,725 A | 6/1992 | Kao |
| 5,120,727 A | 6/1992 | Kao |
| 5,120,842 A | 6/1992 | Failli |
| 5,163,952 A | 11/1992 | Froix |
| 5,177,203 A | 1/1993 | Failli |
| 5,304,121 A | 4/1994 | Sahatjlan |
| 5,355,832 A | 10/1994 | Loh et al. |
| 5,370,614 A | 12/1994 | Amundson |
| 5,447,724 A | 9/1995 | Helmus |
| 5,457,111 A | 10/1995 | Luly |
| 5,464,650 A | 11/1995 | Berg |
| 5,516,781 A | 5/1996 | Morris |
| 5,527,337 A | 6/1996 | Stack |
| 5,563,146 A | 10/1996 | Morris |
| 5,591,195 A | 1/1997 | Taheri et al. |
| 5,591,227 A | 1/1997 | Dinh et al. |
| 5,605,696 A | 2/1997 | Eury |
| 5,624,411 A | 4/1997 | Tuch |
| 5,646,160 A | 7/1997 | Morris |
| 5,649,977 A | 7/1997 | Campbell |
| 5,665,728 A | 9/1997 | Morris |
| 5,705,583 A | 1/1998 | Bowers |
| 5,720,735 A | 2/1998 | Dorros |
| 5,755,771 A | 5/1998 | Penn et al. |
| 5,767,144 A | 6/1998 | Winn |
| 5,843,089 A | 12/1998 | Sahatjian et al. |
| 5,843,172 A | 12/1998 | Yan |
| 5,893,840 A | 4/1999 | Hull et al. |
| 6,015,815 A | 1/2000 | Mollison |
| 6,017,324 A | 1/2000 | Tu et al. |
| 6,033,434 A | 3/2000 | Borghi |
| 6,083,257 A | 7/2000 | Taylor |
| 6,090,901 A | 7/2000 | Bowers |
| 6,106,548 A | 8/2000 | Roubin |
| 6,106,889 A | 8/2000 | Beavers et al. |
| 6,129,705 A | 10/2000 | Grantz |
| 6,146,358 A | 11/2000 | Rowe |
| 6,235,786 B1 | 5/2001 | Dai |
| 6,273,913 B1 | 8/2001 | Wright |
| 6,284,305 B1 | 9/2001 | Ding |
| 6,299,604 B1 | 10/2001 | Ragheb et al. |
| 6,306,144 B1 | 10/2001 | Sydney et al. |
| 6,306,166 B1 | 10/2001 | Barry et al. |
| 6,329,386 B1 | 12/2001 | Mollison |
| 6,335,029 B1 | 1/2002 | Kamath et al. |
| 6,358,556 B1 | 3/2002 | Ding |
| 6,364,856 B1 | 4/2002 | Ding et al. |
| 6,368,658 B1 | 4/2002 | Schwarz et al. |
| 6,406,457 B1 | 6/2002 | Wang |
| 6,413,272 B1 | 7/2002 | Igak |
| 6,419,692 B1 | 7/2002 | Yang |
| 6,500,148 B1 | 12/2002 | Pinchuk |
| 6,521,658 B1 | 2/2003 | Li |
| 6,585,764 B2 | 7/2003 | Wright |
| 6,616,650 B1 | 9/2003 | Rowe |
| 6,669,980 B2 | 12/2003 | Hansen |
| 6,682,553 B1 | 1/2004 | Webler, Jr. |
| 6,682,556 B1 | 1/2004 | Ischinger |
| 6,709,440 B2 | 3/2004 | Callol et al. |
| 6,726,923 B2 | 4/2004 | Iyer et al. |
| 6,991,617 B2 | 1/2006 | Hektner |
| 7,048,714 B2 | 5/2006 | Richter |
| 7,087,263 B2 | 8/2006 | Hossainy et al. |
| 7,241,344 B2 | 7/2007 | Worsham |
| 7,273,417 B1 | 9/2007 | Lundquist |
| 7,357,942 B2 | 4/2008 | Burke et al. |
| 7,378,105 B2 | 5/2008 | Burke et al. |
| 7,396,539 B1 | 7/2008 | Hossainy et al. |
| 7,399,480 B2 | 7/2008 | Mollison et al. |
| 7,445,792 B2 | 11/2008 | Toner et al. |
| 7,455,853 B2 | 11/2008 | Mollison et al. |
| 7,572,245 B2 | 8/2009 | Herweck et al. |
| 8,057,813 B2 | 11/2011 | Toner et al. |
| 2002/0123505 A1 | 9/2002 | Mollison et al. |
| 2002/0183581 A1 | 12/2002 | Yoe et al. |
| 2002/0193828 A1 | 12/2002 | Griffin et al. |
| 2003/0129215 A1 | 7/2003 | Mollison |
| 2003/0170287 A1 | 9/2003 | Prescott |
| 2003/0204238 A1 | 10/2003 | Tedeschi |
| 2003/0216699 A1 | 11/2003 | Falotico |
| 2004/0073284 A1 | 4/2004 | Bates et al. |
| 2004/0224003 A1 | 11/2004 | Schultz |
| 2004/0225345 A1 | 11/2004 | Fischell et al. |
| 2004/0234748 A1 | 11/2004 | Stenzel |
| 2004/0254635 A1 | 12/2004 | Shanley et al. |
| 2004/0267352 A1 | 12/2004 | Davidson et al. |
| 2005/0004661 A1 | 1/2005 | Lewis |
| 2005/0019404 A1 | 1/2005 | Sung et al. |
| 2005/0036946 A1 | 2/2005 | Pathak et al. |
| 2005/0106206 A1 | 5/2005 | Herweck et al. |
| 2005/0149173 A1 | 7/2005 | Hunter et al. |
| 2005/0163818 A1 | 7/2005 | Sung et al. |
| 2005/0163913 A1 | 7/2005 | Spencer et al. |
| 2005/0169957 A1 | 8/2005 | Hossainy |
| 2005/0178396 A1 | 8/2005 | Hunter et al. |
| 2005/0246009 A1 | 11/2005 | Toner et al. |
| 2005/0250672 A9 | 11/2005 | Speck et al. |
| 2006/0020243 A1 | 1/2006 | Speck et al. |
| 2006/0171984 A1 | 8/2006 | Cromack et al. |
| 2006/0198867 A1 | 9/2006 | Toner et al. |
| 2007/0027523 A1 | 2/2007 | Toner et al. |
| 2007/0088255 A1 | 4/2007 | Toner et al. |
| 2007/0224240 A1 | 9/2007 | Toner et al. |
| 2008/0003254 A1 | 1/2008 | Mack et al. |
| 2008/0057101 A1 | 3/2008 | Roorda |
| 2008/0255508 A1 | 10/2008 | Wang |
| 2008/0262589 A1 | 10/2008 | Nagura |
| 2008/0300675 A1 | 12/2008 | Penhasi |
| 2009/0162413 A1 | 6/2009 | Burke et al. |
| 2009/0285974 A1 | 11/2009 | Kerrigan |
| 2010/0023108 A1 | 1/2010 | Toner et al. |
| 2010/0030183 A1 | 2/2010 | Toner et al. |
| 2010/0076377 A1 | 3/2010 | Ehrenreich |
| 2010/0076401 A1 | 3/2010 | Von Oepen |
| 2011/0143014 A1 | 6/2011 | Stankus et al. |
| 2011/0144577 A1 | 6/2011 | Stankus et al. |
| 2011/0144582 A1 | 6/2011 | Stankus et al. |

FOREIGN PATENT DOCUMENTS

| | | |
|---|---|---|
| EP | 0 184 162 | 4/1994 |
| EP | 0 623 354 | 11/1994 |
| WO | WO 92/05179 | 4/1992 |
| WO | WO 01/87372 | 11/2001 |
| WO | WO 03/022324 | 3/2003 |
| WO | WO 2004/022124 | 3/2004 |
| WO | WO 2004/037443 | 5/2004 |
| WO | WO 2005/089855 | 9/2005 |
| WO | WO 2006/024492 | 3/2006 |
| WO | WO 2006/116348 | 11/2006 |
| WO | WO 2007/032777 | 3/2007 |
| WO | WO 2007/046935 | 4/2007 |
| WO | WO 2007/065722 | 6/2007 |
| WO | WO 2007/109372 | 9/2007 |
| WO | WO 2008/021124 | 2/2008 |
| WO | WO 2008/089730 | 7/2008 |
| WO | WO 2009/051614 | 4/2009 |
| WO | WO 2010/027735 | 3/2010 |
| WO | WO 2010/030995 | 3/2010 |
| WO | WO 2010/093799 | 8/2010 |

OTHER PUBLICATIONS

U.S. Appl. No. 12/371,426, Aug. 2, 2012 Applicant Initiated Interview Summary.
U.S. Appl. No. 12/371,426, May 1, 2012 Amendment and Request for Continued Examination (RCE).
U.S. Appl. No. 12/371,426, Apr. 12, 2012 Advisory Action.
U.S. Appl. No. 12/371,426, Apr. 2, 2012 Response to Final Office Action.
U.S. Appl. No. 12/371,426, Mar. 15, 2012 Applicant Initiated Interview Summary.
U.S. Appl. No. 12/371,426, Feb. 1, 2012 Final Office Action.

U.S. Appl. No. 12/371,426, Jan. 5, 2012 Applicant Initiated Interview Summary.
U.S. Appl. No. 12/371,426, Nov. 7, 2011 Response to Non-Final Office Action.
U.S. Appl. No. 12/371,426, Aug. 5, 2011 Non-Final Office Action.
U.S. Appl. No. 12/371,422, Aug. 27, 2012 Supplemental Amendment and Statement of the Substance of Interview.
U.S. Appl. No. 12/371,422, Aug. 1, 2012 Applicant Initiated Interview Summary.
U.S. Appl. No. 12/371,422, Apr. 20, 2012 Amendment and Request for Continued Examination (RCE).
U.S. Appl. No. 12/371,422, Mar. 13, 2012 Applicant Initiated Interview Summary.
U.S. Appl. No. 12/371,422, Jan. 20, 2012 Final Office Action.
U.S. Appl. No. 12/371,422, Dec. 30, 2011 Applicant Initiated Interview Summary.
U.S. Appl. No. 12/371,422, Dec. 22, 2011 Supplemental Amendment.
U.S. Appl. No. 12/371,422, Nov. 7, 2011 Response to Non-Final Office Action.
U.S. Appl. No. 12/371,422, Aug. 5, 2011 Non-Final Office Action.
U.S. Appl. No. 11/084,172, Sep. 23, 2011 Issue Fee payment.
U.S. Appl. No. 11/084,172, Sep. 19, 2011 Notice of Allowance.
U.S. Appl. No. 11/084,172, Jul. 29, 2011 Supplemental Amendment.
U.S. Appl. No. 11/084,172, Jun. 29, 2011 Examiner Interview Summary.
U.S. Appl. No. 11/084,172, Apr. 22, 2010 Amendment and Request for Continued Examination (RCE).
U.S. Appl. No. 11/084,172, Jan. 22, 2010 Final Office Action.
U.S. Appl. No. 11/084,172, Sep. 29, 2009 Response to Non-Final Office Action.
U.S. Appl. No. 11/084,172, Apr. 29, 2009 Non-Final Office Action.
U.S. Appl. No. 11/084,172, Dec. 31, 2008 Amendment and Request for Continued Examination (RCE).
U.S. Appl. No. 11/084,172, Jul. 3, 2008 Final Office Action.
U.S. Appl. No. 11/084,172, Apr. 7, 2008 Response to Non-Final Office Action.
U.S. Appl. No. 11/084,172, Jan. 9, 2008 Non-Final Office Action.
U.S. Appl. No. 11/539,944, Oct. 18, 2012 Applicant Initiated Interview Summary.
U.S. Appl. No. 11/539,944, Aug. 3, 2012 Final Office Action.
U.S. Appl. No. 11/539,944, May 7, 2012 Response to Non-Final Office Action.
U.S. Appl. No. 11/539,944, Apr. 16, 2012 Applicant Summary of Interview with Examiner.
U.S. Appl. No. 11/539,944, Mar. 15, 2012 Applicant Initiated Interview Summary.
U.S. Appl. No. 11/539,944, Feb. 6, 2012 Non-Final Office Action.
U.S. Appl. No. 11/539,944, Aug. 8, 2011 Supplemental Amendment.
U.S. Appl. No. 11/539,944, Jul. 8, 2011 Examiner Interview Summary.
U.S. Appl. No. 11/539,944, Jan. 31, 2011 Amendment and Request for Continued Examination (RCE).
U.S. Appl. No. 11/539,944, Oct. 29, 2010 Final Office Action.
U.S. Appl. No. 11/539,944, Aug. 12, 2010 Response to Non-Final Office Action.
U.S. Appl. No. 11/539,944, May 12, 2010 Non-Final Office Action.
U.S. Appl. No. 11/539,944, Apr. 26, 2010 Summary of Record of Interview and Supplemental Amendment.
U.S. Appl. No. 11/539,944, Mar. 26, 2010 Examiner Interview Summary.
U.S. Appl. No. 11/539,944, Feb. 2, 2010 Amendment and Request for Continued Examination (RCE).
U.S. Appl. No. 11/539,944, Sep. 2, 2009 Final Office Action.
U.S. Appl. No. 11/539,944, Jun. 29, 2009 Response to Non-Final Office Action.
U.S. Appl. No. 11/539,944, Mar. 16, 2009 Non-Final Office Action.
U.S. Appl. No. 11/483,030, Jul. 19, 2012 Final Office Action.
U.S. Appl. No. 11/483,030, May 2, 2012 Response to Non-Final Office Action.
U.S. Appl. No. 11/483,030, Apr. 16, 2012 Applicant Summary of Interview with Examiner.
U.S. Appl. No. 11/483,030, Mar. 15, 2012 Applicant Initiated Interview Summary.
U.S. Appl. No. 11/483,030, Feb. 2, 2012 Non-Final Office Action.
U.S. Appl. No. 11/483,030, Aug. 8, 2011 Supplemental Amendment.
U.S. Appl. No. 11/483,030, Jul. 8, 2011 Examiner interview Summary.
U.S. Appl. No. 11/483,030, Jan. 31, 2011 Amendment and Request for Continued Examination (RCE).
U.S. Appl. No. 11/483,030, Oct. 29, 2010 Final Office Action.
U.S. Appl. No. 11/483,030, Aug. 12, 2010 Response to Non-Final Office Action.
U.S. Appl. No. 11/483,030, May 12, 2010 Non-Final Office Action.
U.S. Appl. No. 11/483,030, Apr. 26, 2010 Applicant Summary of Interview with Examiner.
U.S. Appl. No. 11/483,030, Mar. 26, 2010 Examiner Interview Summary.
U.S. Appl. No. 11/483,030, Feb. 2, 2010 Amendment and Request for Continued Examination (RCE).
U.S. Appl. No. 11/483,030, Sep. 2, 2010 Final Office Action.
U.S. Appl. No. 11/483,030, Jun. 29, 2009 Response to Non-Final Office Action.
U.S. Appl. No. 11/483,030, Mar. 31, 2009 Non-Final Office Action.
U.S. Appl. No. 12/636,124, Oct. 22, 2012 Applicant Initiated Interview Summary.
U.S. Appl. No. 12/636,124, Oct. 22, 2012 Final Office Action.
U.S. Appl. No. 12/636,124, Jul. 16, 2012 Response to Non-Final Office Action.
U.S. Appl. No. 12/636,124, Mar. 15, 2012 Non-Final Office Action.
U.S. Appl. No. 12/636,079, Aug. 27, 2012 Applicant Summary of Interview with Examiner.
U.S. Appl. No. 12/636,079, Jul. 26, 2012 Applicant Initiated Interview Summary.
U.S. Appl. No. 12/636,158, Oct. 23, 2012 Amendment and Request for Continued Examination (RCE).
U.S. Appl. No. 12/636,158, May 23, 2012 Final Office Action.
U.S. Appl. No. 12/636,158, Mar. 12, 2012 Response to Non-Final Office Action.
U.S. Appl. No. 12/636,158, Oct. 12, 2011 Non-Final Office Action.
U.S. Appl. No. 12/090,253, Jun. 1, 2012 Final Office Action.
U.S. Appl. No. 12/090,253, Apr. 9, 2012 Response to Non-Final Office Action.
U.S. Appl. No. 12/090,253, Dec. 8, 2011 Non-Final Office Action.
U.S. Appl. No. 11/548,827, Oct. 5, 2012 Terminal Disclaimer Review Decision.
U.S. Appl. No. 11/548,827, Oct. 4, 2012 Terminal Disclaimer Filed.
U.S. Appl. No. 11/548,827 Aug. 7, 2012 Preliminary Amendment and Summary of the Interview.
U.S. Appl. No. 11/548,827, Aug. 2, 2012 Applicant Initiated Interview Summary.
U.S. Appl. No. 11/548,827, Aug. 3, 2011 Amendment and Request for Continued Examination (RCE).
U.S. Appl. No. 11/548,827, May 3, 2011 Final Office Action.
U.S. Appl. No. 11/548,827, Mar. 1, 2011 Response to Non-Final Office Action.
U.S. Appl. No. 11/548,827, Oct. 1, 2011 Non-Final Office Action.
U.S. Appl. No. 11/548,827, Apr. 28, 2010 Request for Continued Examination (RCE).
U.S. Appl. No. 11/548,827, Apr. 21, 2010 Advisory Action.
U.S. Appl. No. 11/548,827, Mar. 25, 2010 Response to Final Office Action.
U.S. Appl. No. 11/548,827, Feb. 3, 2010 Supplemental Final Office Action.
U.S. Appl. No. 11/548,827, Jan. 25, 2010 Final Office Action.
U.S. Appl. No. 11/548,827, Oct. 12, 2009 Response to Notice Non-Complaint.
U.S. Appl. No. 11/548,827, Sep. 23, 2009 Notice of Non-Complaint.
U.S. Appl. No. 11/548,827, Sep. 18, 2009 Terminal Disclaimer Review Decisiom.
U.S. Appl. No. 11/548,827, Aug. 14, 2009 Respponse to Non-Final Office Action and Terminal Disclaimer filed.
U.S. Appl. No. 11/548,827, May 29, 2009, Non-Final Office Action.

Heldman, et al., "Paclitaxel stent coating inhibits neointimal hyperplasia at 4 weeks in a porcine model of coronary restenosis", *Circulation*, 103(18):2289-95 (2001).

Reil et al., Journal of Surgical Research, 1999, 85: 109-114.

Roberge et al., Ocular Immunology and Inflammation, 1995, 3: 195-202.

Burke et al., "Zotarolimus (ABT-578) eluting stents", *Advanced Drug Delivery Reviews*, Mar. 6, 2006, 58: 437-446.

International Search Report for PCT/US2005/009310, Jul. 2005.

International Search Report for PCT/US2006/040027, Sep. 2007.

International Search Report for PCT/US2007/021846, Mar. 2009.

International Search Report and Written Opinion for PCT/US2010/055806, Mar. 2011.

Partial International Search Report for PCT/US2010/055809, May 2011.

International Search Report and Written Opinion for PCT/US2010/055818, Feb. 2011.

International Search Report and Written Opinion for PCT/US2010/023907, Jun. 2010.

European Search Report issued on Mar. 1, 2011 in application No. EP10011851.2. (corresponding to US 2010/0030183A1).

Aggarwal, A., D.J. Schneider, B.E. Sobel, and H.L. Dauerman. 2003. "Comparison of inflammatory markers in patients with diabetes mellitus versus those without before and after coronary arterial stenting." *Am J Cardiol.* 92:924-9.

Baker, H., A. Sldorowicz, S.N. Sehgal, and C. Vezina. 1978. "Rapamycin (AY-22,989), a new antifungal antibiotic. III. In vitro and in vivo evaluation." *J Antibiot* (Tokyo). 31 :539-45.

Bierer, B.E., S.L. Schreiber, and S.J. Burakoff. 1991. "The effect of the immunosuppressant FK-506 on alternate pathways of T cell activation." *Eur J Imrnuno.* 21:439-45.

Biondi-Zoccai, G.G., A. Abbate, G. Liuzzo, and L.M. Biasucci. 2003. "Atherothrornbosis, Inflarnmation, and diabetes.". *J Am Coll Cardiol.* 41 :1071-7.

Boland et al. *International Journal of Cardiovascular Interventions*, 2000, 3:215-225.

B, Braun Melsungen A.G. Press release, "Drug-Coated ballon overcomes in stent retenosis," Apr. 2, 2008 *B Braum Melsungnen A.G. website*. Downloaded from <http://www.bbraun.com/cps/rde/xchg/bbraun-com/hs.xsl/news_drug-coated-ballon-overcomes-in-stent-restenosis.html?from=newssearch> on Sep. 28, 2010.

Brown, E.J., M.W. Albers, T.B. Shin, K. Ichikawa, C.T. Keith, W.S. Lane, and S.L. Schreiber. 1994. "A mammalian protein targeted by GI-arresting rapamycin-receptor complex." *Nature.* 369:756-8.

Bunchman, T.E., and C.A. Brookshire. 1991. "Smooth muscle cell proliferation by conditioned media from cyclosporinetreated endothelial cells: a role of endothelin." *Transplant Proc.* 23:967-8.

Carter, A.J., M. Aggarwal, G.A. Kopia, F. Tio, P.S. Tsao, R. Kolata, A.C. Yeung, G. Llanos, J. Dooley, and R. Falotico.2004. "Long-term effects of polymer-based, slow-release, sirolimus-eluting stents in a porcine coronary model." *Cardiovasc Res.* 63:617-24.

Cremers, et al., "Inhibition of Coronary Neointimal Hyperplasia in Swine Using a Novel Zotarolimus-Eluting Balloon Catheter", *European Society of Cardiology*, XP002616155, Aug. 31, 2009, URL:HTTP://spo.escardio.org/eslides/view.aspx?eevtid=33&fp=3206.

Dandona, P., and A. Aljada. 2002. "A rational approach to pathogenesis and treatment of type 2 diabetes mellitus, insulin resistance, inflammation, and atherosclerosis." *Am J Cardiol.* 90:27G-33G.

Dumont, F.J., M.R. Melino, M.J. Staruch, S.L. Koprak, P.A. Fischer, and N.H. Sigal. 1990. The immunosuppressive macrolides FK-506 and rapamycin act as reciprocal antagonists in murine T cells. J Immunol. 144:1418-24.

Fretz, H., M. Albers, A. Gala, R. Standaert, W. Lane, S. Burakoff, B. Bierer, and S. Schreiber. 1991. "Rapamycin and FK506 binding proteins (immunophilins)." *J Am. Chem. Soc.* 113:1409-1411.

Grech, E.D., and D.R. Ramsdale. 2003. "Acute coronary syndrome: unstable angina and non-ST segment elevation myocardial infarction." *British Med. J.* 326:1259-61.

Harding, M.W., A. Galat, D.E. Uehling, and S.L. Schreiber. 1989. "A receptor for the immunosuppressant FK506 is a cis-trans peptidyl-proyl isomerase." *Nature*, 341:758-60.

Hayward, C., D. Yohannes, and S. Danishefsky. 1993. "Total synthesis of rapamycin via a novel titanium-mediated aldol macrocyclization reaction." *J. Am. Chem. Soc.* 11.5:9345-9346.

Helmus, M. 1990. "Medical Device Design—A Systems Approach: Central Venous Catheters." In 22nd International Society for the Advancement of Material and Process Engineering Technical Conference.

Ji, Q., M. Reimer, and T. El-Shourbagy. 2004. "96-well liquid-liquid extraction liquid chromatography-tandem mass spectrometry method for the quantitative determination of ABT-578 in human blood samples." *Journal of Chromatography* B. 805:67-75.

Kino, T., N. Inamura, F. Sakai, K. Nakahara, T. Goto, M. Okuhara, M. Kohsaka, H Aoki, and T. Ochiai. 1987. "Effect of FK-506 on human mixed lymphocyte reaction in vltro." *Transplant Proc.* 19:36-9.

Kornowski, R., M.K. Hong, F.O. Tio, O. Bramwell, H. Wu, and M.B. Leon. 1998. "In-stent restenosis: contributions of inflammatory responses and arterial injury to neointimal hyperplasia." *J Am Coll Cardiol.* 31:224-30.

Levin et al., "Specific binding to intracellular proteins determines arterial transport properties for rapamycin and paclitaxel." *PNAS* vol. 101, No. 25, pp. 9463-9467 (2004).

Martel, R.R., J. Klicius, and S. Galet. 1977. "Inhibition of the immune response by rapamycin, a new antifungal antibiotic." *Can J Physiol Pharmacol.* 55:48-51.

Morris, R. 1992. "Rapamycins: antifungal, antitumor, antiproliferative, and immunosuppressive macrolides." *Transplant. Rev.* 6:39-87.

Morris, R., and B. Meiser. 1989. "Identification of a new pharmacologic action for an old compound." *Med. Sci. Res.* 17:609-610.

Nicolaou, K., T. Chakraborty, A. Piscopio, N. Minowa, and P. Bertinato. 1993. "Total synthesis of rapamycin." *J. Am. Chem. Soc.* 115:4419-4420.

Paiva, N.L., A.L. Demain, and M.F. Roberts. 1991. "Incorporation of acetate, propionate, and methionine into rapamycin by *Streptomyces hygroscopicus.*" *J Nat Prod.* 54:167-77.

Richard, et al., "Controlled Delivery of Paclitaxel from stent Coatings Using Novel Styrene Maleic Anhydride Copolymer Formulations", *Journal of Biomedical Materials Research*, vol. 90A, No. 2, pp. 522-523, Jun. 18, 2008, www.interscience.wiley.com.

Roffi, M., and E.J. Topol. 2004. "Percutaneous coronary intervention in diabetic patients with non-ST-segment elevation acute coronary syndromes." *Eur Heart J.* 25:190-8.

Romo, D., S. Meyer, D. Johsnon, and S. Schrieber. 1993. "Total synthesis of (-)-rapamycin using an Evans-Tishchenko fragment coupling." *J. Am. Chem. Soc.* 115:7906-7907.

Sabatini, D.M., H. Erdjument-Bromage, M. Lui, P. Tempst, and S.H. Snyder. 1994. "RAFTI: a mammalian protein that binds to FKBPIZ in a rapamycin-dependent fashion and is homologous to yeast TORS." *Cell.* 78:35-43.

Salem et al. *International Archives of Allergy and Immunology*, 2000 121:235-245.

Schwartz, R. et al., 1992. "Restenosis and the proportional neointimal response to coronary artery injury: results in a porcine model." *J Am Coll Cardiol.* 19:267-274.

Sehgal, S.N., H. Baker, C.P. Eng, K. Singh, and C. Vezina. 1983. "Demethoxyrapamycin (AY-24,668), a new antifungal antibiotic." *J Antibiot* (Tokyo). 36:351-4.

Sehgal, S.N., H. Baker, and C. Vezina. 1975. "Rapamycin (AY-22,989), a new antifungal antibiotic. II. Fermentation, isolation and characterization." *J Antibiot* (Tokyo). 28:727-32.

Shichiri, M., Y. Hirata, T. Nakajima, K. Ando, T. Imai, M. Yanagisawa, T. Masaki, and F. Marumo. 1991. "Endothelin-I is an autocrine/paracrine growth factor for human cancer cell lines." *J Clin Invest.* 87:1867-71.

Siekierka, J.J., S.H. Hung, M. Poe, C.S. Lin, and N. H. Sigal. 1989. "A cytosolic binding protein for the immunosuppressant FK506 has peptidyl-prolyl isomerase activity but is distinct from cyclophilin." *Nature.* 341 :755-7.

Stella, "A Case for Prodrugs in Prodrugs: Challenges and Rewards Part I," Eds. Stella et al. New York: Springer, 2007. 1-33.

Stiles, "Paclitaxel-coated balloon cuts late lumen loss after PCI for in-stent restenosis," *The Heart.org from WebMD*, Apr. 4, 2008. Downloaded from <http://www.theheart.org/article/855221/print.do> on Sep. 28, 2009.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tio, P.S. Tsao, R. Falotico, and A.J. Carter. 2001. "Stent-based delivery of sirolimus reduces neointimal formation in a porcine coronary model." *Circulation.* 104:1188-93.

Unverdorben et al., 2009, "Paclitaxel-coated balloon catheter versus paclitaxel-coated stent for the treatment of coronary in-stent restenosis." *Circulation* 119:2986-2994.

Van der Hoeven et al., "Drug-eluting stents: results, promises and problems," *Int. J of Cardiology* 99, pp. 9-17 (2005).

Vezina, C., A. Kudelski, and S.N. Sehgal. 1975. "Rapamycin (AY-22,989), a new antifungal antibiotic. I. Taxonomy of the producing streptomycete and isolation of the active principle." *J Antibiot* (Tokyo). 28:721-6.

Wei et al. *Journal of Cardiothoracic and Vascular Anesthesia*, 2001, 4:455-459,.

Yamagishi, S., C.C. Hsu, K. Kobayashi, and H. Yamamoto. 1993. "Endothelin 1 mediates endothelial cell-dependent proliferation of vascular pericytes." *Biochem Biophys Res Commun.* 191:840-6.

Yudkin, J.S., M. Kumari, S.E. Humphries, and V. Mohamed-Ali. 2000. "Inflammation, obesity, stress and coronary heart disease: is interleukin-6 the LINK?" *Atherosclerosis.* 148:209-14.

U.S. Appl. No. 11/548,827, Dec. 24, 2012 Examiner Initiated Interview Summary.

U.S. Appl. No. 11/548,827, Nov. 9, 2012 Notice of Allowance.

U.S. Appl. No. 12/371,422, Dec. 20, 2012 Notice of Allowance.

U.S. Appl. No. 12/090,253, Dec. 28, 2012 Notice of Abandonment.

U.S. Appl. No. 12/636,124, Dec. 21, 2012 Response to Final Office Action.

U.S. Appl. No. 12/371,422, Mar. 20, 2013, Issue Fee payment.

U.S. Appl. No. 12/636,079, Apr. 18, 2013, Non-Final Office Action.

U.S. Appl. No. 12/636,124, Mar. 6, 2013, Notice of Allowance.

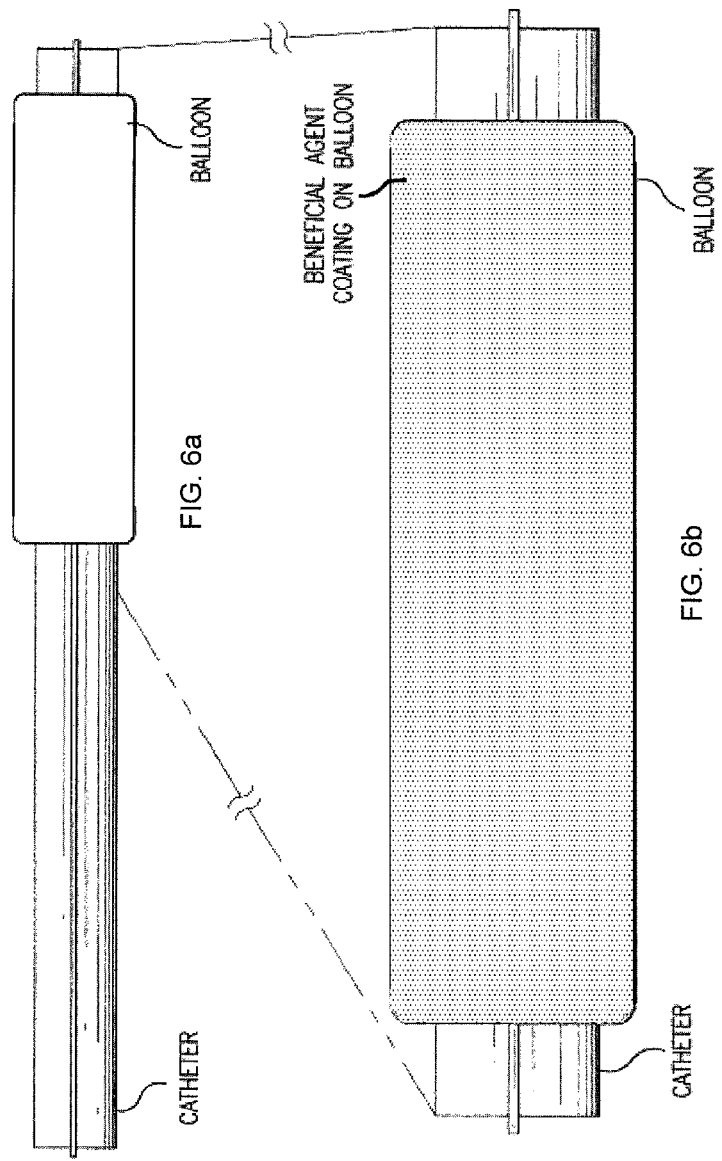

Graph II Summary of Results of Late Lumen Loss [mm] Assessed By QCA

Graph III Results of Neointimal Area [mm] assessed by Histomorphometry

MULTIPLE DRUG DELIVERY FROM A BALLOON AND A PROSTHESIS

CROSS-REFERENCE TO RELATED APPLICATIONS

The present applications is a continuation of Ser. No. 12/371,422, filed Feb. 13, 2009, which is a continuation-in-part of U.S. patent application Ser. No. 11/084,172, filed Mar. 18, 2005, now U.S. Pat. No. 8,057,813, which claims priority to U.S. Provisional Application No. 60/554,730, filed on Mar. 19, 2004, each of which are hereby incorporated in their entirety by reference.

BACKGROUND OF THE INVENTION

1. Related Application

The present invention relates to an interventional device for delivery of therapeutic agents from an angioplasty balloon and from a prosthesis such as an intraluminal stent. The invention also relates to the method of loading the beneficial agents onto the balloon and the medical device, as well as the method of delivery of the agents from separate surfaces. The invention also relates to an interventional device having a prosthesis surface that is loaded with a first beneficial agent, and a balloon surface loaded with a second beneficial agent. The invention also relates to a method of loading multiple beneficial agents onto the prosthesis surfaces and the balloon surfaces, and to a method of manufacturing an interventional device for the delivery of a first beneficial agent and a second beneficial agent from separate surfaces.

2. Description of Related Art

Balloon angioplasty associated with the implantation of a vascular stent is a procedure designed to expand occluded blood vessels, resulting in adequate perfusion of distal tissues. The stent, which is crimped onto the balloon, is introduced via a peripheral artery, and advanced to the lesion site over a guidewire. Inflation of the balloon results in compression of plaque and simultaneous implantation of the stent, which acts as a scaffold to keep the vessel expanded to its normal diameter. The balloon is then deflated, allowing removal of the catheter assembly, leaving the stent in place to maintain patency of the vessel.

This percutaneous intervention, described as PCI when associated with coronary balloon angioplasty, has been effective in normalizing the vessel lumen, and providing relief of pain often associated with myocardial ischemia. The procedure is not restricted to the coronary vasculature, but may also be applied to other vessels, including renal, carotid, iliac and superficial femoral arteries. However, although the success of the intervention is generally high, the long-term patency of the vessel is often reduced by restenosis of the vessel at the site of the original lesion. This restenotic process is the consequence of a variety of factors acting in concert to re-occlude the vessel, reducing blood flow and nutrient supply to tissues. These include progression of the underlying disease, as well as the generation of cytokines and other growth factors which promote cell proliferation. These factors emanate from a variety of inflammatory cell types including monocytes and macrophages. In addition to inflammation and cell proliferation, migration of cells from the medial or adventitial layers of the vessel wall may contribute to the growth of a new layer, described as neointima, which re-occludes the vessel. In recent years, the use of bare metal stents, while effective in the short-term, has been associated with a significant rate of restenosis. Therefore, many investigators have sought to provide technologies to reduce the restenosis rate, while maintaining the beneficial effects offered by these metal scaffolds. The coating of stents with bioinert polymers has been somewhat effective, but the most important advance in this field has been the loading of these polymers with drugs known to block cell proliferation. One commonly applied technique for the local delivery of a drug is through the use of a polymeric carrier coated onto the surface of a stent, as disclosed in Berg et al., U.S. Pat. No. 5,464,650, the disclosure of which is incorporated herein by reference. Such conventional methods and products generally have been considered satisfactory for their intended purpose. The gradual elution of drug from the polymer is known to impact the restenotic process, providing beneficial concentrations of the beneficial agent at a time when the inflammatory and proliferative processes are thought to be most prevalent. The introduction of these drug-eluting stents (DES) has reduced the restenosis rate from 20-30% to less than 10% in several clinical trials. However, many are attempting to reduce the rate even further, providing nearly all patients who receive a DES with long-term vessel patency and minimal chance of return to the cath lab for repeat procedures. The delivery of multiple drugs, using both the stent and the balloon itself as delivery platforms, may help to achieve this goal.

As evident from the related art, conventional methods of loading interventional devices with beneficial agents, such as drugs, often requires coating the entire prosthesis with a polymer capable of releasing beneficial drugs, as disclosed in Campbell, U.S. Pat. No. 5,649,977 and Dinh et al., U.S. Pat. No. 5,591,227, the disclosures of which are incorporated by reference.

Therefore, the present invention proposes the use of one or more beneficial agents, applied to the surface of the balloon material by any method, and the application of one or more beneficial agents applied to either the bare-metal surface of a second device, or incorporated with the polymer which coats the second device. The delivery of the beneficial agent from the balloon is expected to occur during either pre-dilatation of the vessel at the lesion site, or from the balloon during the delivery of the device during a stenting procedure. Additionally, the delivery of the beneficial agent can be from the balloon during a final stent sizing balloon expansion. The delivery of the beneficial agent from the prosthesis is expected to occur over a longer period, as the drug is released from the polymer or from the surface of the device. The associated prosthesis may be placed directly when the balloon is inflated at the lesion site, immediately after as commonly practiced in pre-dilatation procedures, or within a suitable time period in a second interventional procedure.

SUMMARY OF THE INVENTION

The purpose and advantages of the present invention will be set forth in and apparent from the description that follows, as well as will be learned by practice of the invention.

Additional advantages of the invention will be realized and attained by the methods and systems particularly pointed out in the written description and claims hereof, as well as from the appended drawings.

According to one embodiment, the present invention relates to a system for delivering a beneficial agent. The system includes a balloon having a coating loaded with a beneficial agent (such as a drug) and a prosthesis having a coating loaded with a beneficial agent (which can also be a drug that is the same or different than the beneficial agent on the balloon.) The balloon and the prosthesis can have more than one beneficial agent in the respective coatings. The coatings can be continuous over the surface of the balloon or the prosthesis or discontinuous. Numerous beneficial agents are suitable for delivery according to the invention.

According to another embodiment, the present invention relates to methods of treating and preventing a vascular disease. The inventive methods include delivery of a balloon having a coating loaded with a beneficial agent and delivery of a prosthesis having a coating loaded with a beneficial agent. The delivery of the balloon and the prosthesis to a target site can be sequential or simultaneous. The coated prosthesis can be delivered before or after the coated balloon. The beneficial agents delivered from the balloon can be the same as or different from those delivered from the stent.

According to other embodiments, the present invention relates to a method of providing a device for treatment and prevention of vascular disease, including techniques for coating the balloon with beneficial agents.

To achieve these and other advantages and in accordance with the purpose of the invention, as embodied and broadly described, the invention includes an interventional device for the delivery of multiple beneficial agents wherein the device comprises a prosthesis to be deployed in a lumen, the prosthesis having a surface; a first beneficial agent loaded on the surface of the prosthesis; and a balloon to expand the prosthesis; and a second beneficial agent loaded on the surface of the balloon.

In a further aspect of the invention, the first beneficial agent and the second beneficial agent can be incompatible with each other or detrimental to each other. The first beneficial agent can be dissolved in a first solvent and the second beneficial agent can be dissolved in a second solvent, wherein the first solvent and the second solvent are immiscible. Similarly, the first beneficial agent can react with the second beneficial agent. It is possible for the first beneficial agent to be more hydrophobic than the second beneficial agent. Also, the first beneficial agent can be loaded along a first controlled trajectory on the prosthesis and the second beneficial agent can be loaded along a second controlled trajectory on the balloon.

In a further aspect of the invention, an interventional device is provided wherein at least one of the first beneficial agent and the second beneficial agent is mixed with a binder prior to being loaded on the prosthesis or the balloon.

In accordance with another aspect of the invention, an interventional device is provided wherein the first beneficial agent is mixed with a binder having a first release rate for delivery of the first beneficial agent from the prosthesis. The second beneficial agent can be mixed with a binder having a second release rate for delivery of the second beneficial agent from the balloon; the first release rate being different than the second release rate. The first beneficial agent can be different than the second beneficial agent.

In accordance with another aspect of the invention, an interventional device is provided wherein the first beneficial agent has a first local areal density and the second beneficial agent has a second local areal density. At least one of the first local areal density and the second local areal density can be uniform across a selected portion of the prosthesis or balloon. Also, at least one of the first local areal density of beneficial agent and the second local areal density can be varied across a selected portion of the prosthesis or balloon. The first local areal density of the first beneficial agent can be different than the second local areal density of the second beneficial agent. The interventional device can further include a third beneficial agent loaded on at least one of the first surface and second surface of the prosthesis or on the balloon.

In accordance with still another aspect of the invention, an interventional device is provided wherein the prosthesis further includes a layer of base material on a selected portion thereof, and the first beneficial agent is loaded to the base material layer. The base material layer defines a pattern for loading the first beneficial agent. This prosthesis is then combined with a balloon that is coated with a second beneficial agent.

In accordance with a further aspect of the invention, the prosthesis includes at least one cavity defined therein. The cavity can be filled with multiple beneficial agents. Preferably, the at least one cavity is at least partially loaded with a base material, and multiple beneficial agents are loaded to the base material. This prosthesis is then combined with a balloon that is coated with a second beneficial agent.

The invention also provides a method of loading multiple beneficial agents onto a prosthesis for delivery within a lumen wherein the method comprises the steps of providing a prosthesis to be deployed within a lumen; providing a first beneficial agent and to be loaded on the prosthesis; providing an additional beneficial agent to be loaded on the prosthesis. This prosthesis is then combined with a balloon that is coated with a second beneficial agent.

In accordance with a further aspect of the invention, the first beneficial agent provided by the first beneficial agent providing step is incompatible with the second beneficial agent provided by the second beneficial agent providing step. The first beneficial agent provided by the first beneficial agent providing step can be dissolved in a first solvent and the second beneficial agent provided by the second beneficial agent providing step can be dissolved in a second solvent. The first solvent and the second solvent can be immiscible. The first beneficial agent provided by the first beneficial agent providing step also can be reactive with the second beneficial agent provided by the second beneficial agent providing step. Furthermore, the dispensing steps can be performed to define an interspersed pattern of the first beneficial agent on the prosthesis and the second beneficial agent on the balloon, if desired. The dispensing steps are performed simultaneously. The dispensing steps also can be performed to define an overlapping pattern of the first beneficial agent and the second beneficial agent.

In accordance with another aspect of the invention, the method can further include the step of mixing the first beneficial agent with a binder prior to the first beneficial agent dispensing step onto the prosthesis and a step of mixing the second beneficial agent with a binder prior to the second beneficial agent dispensing step onto the balloon. In accordance with a still further aspect of the invention, the method can further include the step of mixing the first beneficial agent with a first binder having a first release rate for delivery of the first beneficial agent from the prosthesis and the second beneficial agent with a second binder having a second release rate for delivery of the second beneficial agent from the balloon. The first release rate can be different than the second release rate, and first beneficial agent can be different than the second beneficial agent.

In accordance with another aspect of the invention, a method is provided wherein the first beneficial agent dispensing step is performed to provide the first beneficial agent with a first local areal density and the second beneficial agent dispensing step is performed to provide the second beneficial agent with a second local areal density, wherein at least one of the first local areal density and the second local areal density is varied across a selected portion of the prosthesis or balloon.

In accordance with still another aspect of the invention, a method can be provided further including the step of applying a layer of base material on a selected portion of the prosthesis, and the dispensing steps are performed to introduce the first beneficial agent to the base material layer. The base material layer can be applied to define a pattern for loading the first beneficial agent. This prosthesis is then combined with a balloon that is coated with a second beneficial agent.

The invention also includes an interventional device for delivery of beneficial agent, where the beneficial agent can be selected from a group consisting of antithrombotics, anticoagulants, antiplatelet agents, anti-lipid agents, thrombolytics, antiproliferatives, anti-inflammatories, agents that inhibit hyperplasia, smooth muscle cell inhibitors, antibiotics, growth factor inhibitors, cell adhesion inhibitors, cell adhesion promoters, antimitotics, antifibrins, antioxidants, antineoplastics, agents that promote endothelial cell recovery, antiallergic substances, radiopaque agents, viral vectors, antisense compounds, oligionucleotides, cell permeation enhancers, angiogenesis agents, and combinations thereof. The prosthesis can be a stent, graft, or stent-graft. The prosthesis may also be a vascular or biliary stent or an embolic capture device. The interventional device can include an overcoat applied to at least one of the inner surface or the outer surface of the prosthesis. The prosthesis coating or balloon coating can be applied by dip coating, spray coating, or ink jetting where the fluid-dispenser can be a drop-on-demand fluid type printer or a charge-and-deflect type print head. Additionally, the beneficial agent can be built up on the prosthesis or balloon by applying multiple layers. Furthermore, the beneficial agent can be mixed with a binder and also can be loaded onto the prosthesis with a polymer. The polymer is preferably biocompatible. For example, the polymer can be a macromolecule containing pendant phosphorylcholine groups such as poly($MPC_w$:$LMA_x$:$HPMA_y$:$TSMA_z$), where MPC is 2 methacryoyloxyethylphosphorylcholine, LMA is lauryl methacrylate, HPMA is hydroxypropyl methacrylate and TSMA is trimethoxysilylpropyl methacrylate. The binder can be composed of complex sugars (mannitol), starches (e.g., cellulose), collagens. In general the binder would be noncrystalline, have low water solubility, have good film forming characteristics, good solubility with solvents that may be used to dissolve the drug, biocompatible, inert (non-reactive with respect to the drug and also body tissues, fluids, etc), polymer, (e.g., hydrogel), can be hydrophobic if not hydrogel, especially if it is not permanently attached to balloon (if permanently attached, then can use hydrogel, can be used to absorb drug and then when balloon inflated, will squeeze out the drug into ablumenal tissue), low blood solubility if not permanently attached to balloon In accordance with another aspect of the invention, the beneficial agents can be applied to the interventional device using a fluid jet dispenser capable of dispensing discrete droplets along a controlled trajectory, such as drop-on-demand fluid type printer or a charge-and-deflect type printer. In accordance with a further aspect of the invention, the beneficial agent can be mixed with a binder. The beneficial agent preferably is loaded onto the prosthesis with a polymer. Preferably, the polymer is a phosphorylcholine material. The second beneficial agent preferably is loaded onto the balloon with a nonpolymer film forming excipient.

In yet another aspect of the invention, the prosthesis has a tubular body when deployed, wherein the tubular body defines a longitudinal axis. The first surface of the prosthesis is defined as an inner surface of the tubular body, and the second surface of the prosthesis is defined as an outer surface of the tubular body.

In yet another aspect of the invention, the balloon is loaded with the second beneficial agent such that the delivery of the second agent extends beyond the proximal and distal ends of the prosthesis.

In yet another aspect of the invention, the balloon is loaded with the second beneficial agent such that the delivery of the second agent is delivered in a burst fashion to delivery high drug concentration locally to the tissue very rapidly, whereas the beneficial agent delivered from the prosthesis may be delivered over a longer time frame.

In further accordance with the invention, the first surface is loaded with beneficial agent selected from a group consisting of antiplatelet agents, aspirin, cell adhesion promoters, agents that promote endothelial healing, agents that promote migration and estradiol. The second beneficial agent can be selected from a group consisting of anti-inflammatories, anti-proliferatives, smooth muscle inhibitors, cell adhesion promoters, and the rapamycin analog, ABT-578, i.e., 3S,6R,7E,9R,10R,12R,14S,15E,17E,19E,21S,23S,26R,27R,34aS)-9,10,12,13,14,21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H-pyrido[2,1-c][1,4]oxaazacyclo-hentriacontine-1,5,11,28,29(4H,6H,31H)-pentone.

In accordance with another aspect of the invention, an interventional device is provided wherein the first surface of the prosthesis is defined by a plurality of interconnecting structural members and prosthesis includes a first selected set of the structural members and the second surface of the prosthesis includes a second selected set of the structural members. At least one of the first selected set of structural members and the second selected set of structural members can define at least one ring-shaped element extending around a circumference of the tubular body.

The invention also provides a method of manufacturing an interventional device for the delivery of beneficial agent where the method comprises the steps of providing a prosthesis to be deployed in a lumen, the prosthesis having a first surface and a second surface; providing a first beneficial agent to be delivered from the prosthesis; providing a second beneficial agent to be delivered from the balloon; loading the first beneficial agent to at least a portion of the first surface of the prosthesis; and loading the second beneficial agent to at least a portion of the balloon.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

FIG. 6a is a schematic representation of a balloon catheter. FIG. 6b shows a blowup of the balloon catheter with the shading on the balloon representing a coating of a beneficial agent.

DETAILED DESCRIPTION OF THE PREFERRED EMBODIMENTS

Figure 1:
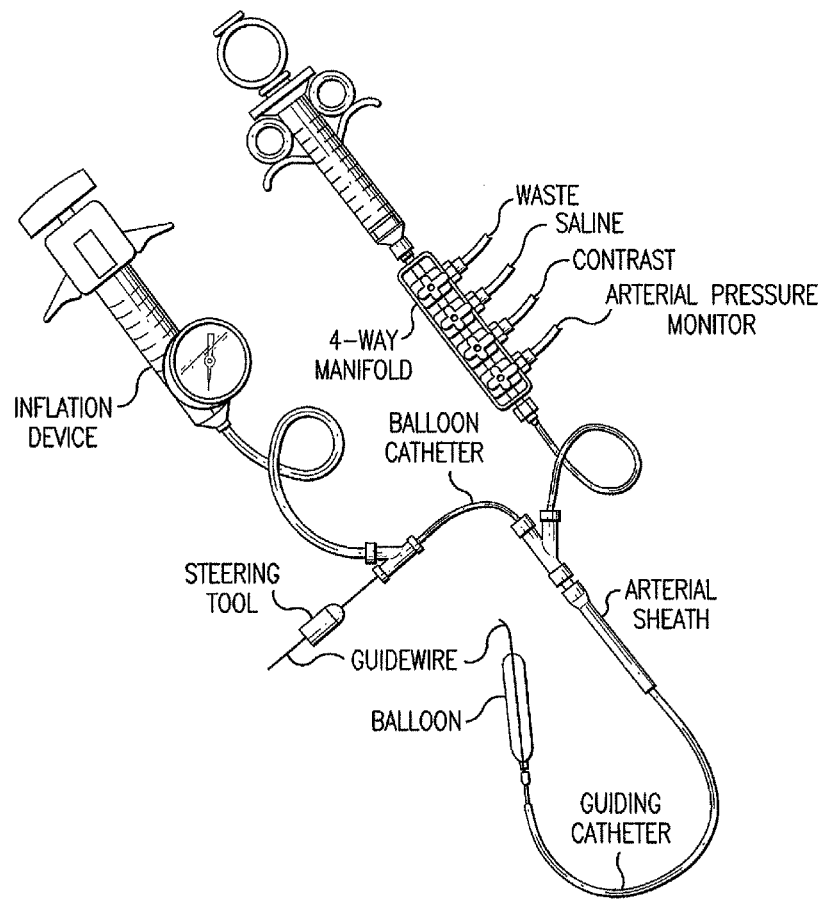
FIG. 1 is a schematic representation of an angioplasty procedure and stent placement equipment showing a balloon on a catheter and the syringe systems used to inflate the balloon.

Reference will now be made in detail to the present preferred embodiments of the method and system for loading a first beneficial agent onto a prosthesis, and a second beneficial agent onto a balloon. Wherever possible, the same reference characters will be used throughout the drawings to refer to the same or like parts.

In accordance with the present invention, a system is provided for delivery of beneficial agents within a lumen. Particularly, the present invention provides a system including a prosthesis having a first beneficial agent and a balloon having second beneficial agent where the beneficial agents are delivered for treatment and prevention of vascular or other intraluminal diseases.

As used herein "interventional device" refers broadly to any device suitable for intraluminal delivery or implantation. For purposes of illustration and not limitation, examples of such interventional devices include stents, grafts, stent-grafts, and the like. As is known in the art, such devices may comprise one or more prostheses, each having a first cross-sectional dimension or profile for the purpose of delivery and a second cross-sectional dimension or profile after deployment. Each prosthesis may be deployed by known mechanical techniques such as balloon expansion deployment techniques, or by electrical or thermal actuation, or self-expansion deployment techniques, as well known in the art. Examples of such for purpose of illustration include U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, all of which are incorporated herein by reference.

Figure 2:
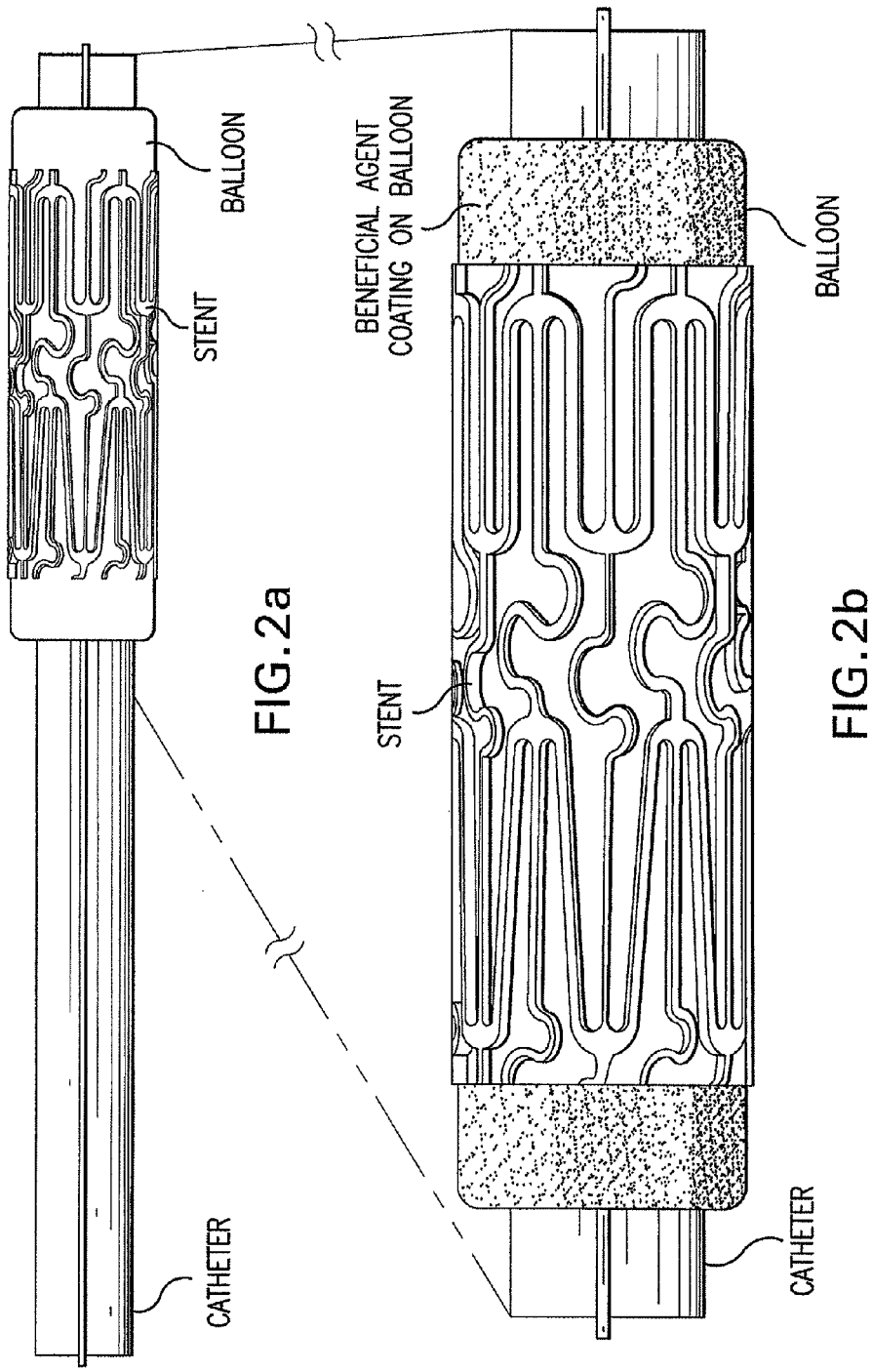
FIG. 2a is a schematic representation of a stent crimped onto a catheter balloon.
FIG. 2b shows a blowup of the balloon and stents section of the catheter with the shading on the balloon representing a coating of a second beneficial agent and the shading of the stent struts representing a coating of a first beneficial agent.

For purposes of explanation and illustration, and not limitation, an exemplary embodiment of the interventional device in accordance with the invention is shown schematically in FIG. 2. In accordance with one aspect of the invention, as shown schematically in FIG. 2, the interventional device generally includes a prosthesis loaded with beneficial agent to provide a local delivery of a first beneficial agent across a treatment zone and a balloon with a second beneficial agent delivered a cross a second overlapping treatment zone. Particularly, as embodied herein the prosthesis may be a stent, a graft or a stent-graft, as previously noted, for intravascular or coronary delivery and implantation. However, the prosthesis may be any type of implantable member capable of being loaded with beneficial agent. The balloon may be any type of catheter based expandable entity that can act to expand the prosthesis, the local tissue, or push the second beneficial agent against the lumen wall.

The prosthesis can be in an expanded or unexpanded state during the loading of beneficial agent. The underlying structure of the prosthesis can be virtually any structural design and the prosthesis can be composed any suitable material such as, but not limited to, stainless steel, "MP35N," "MP20N," elastinite (Nitinol), tantalum, nickel-titanium alloy, platinum-iridium alloy, gold, magnesium, polymer, ceramic, tissue, or combinations thereof. "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. The prosthesis can be made from bioabsorbable or biostable polymers. In some embodiments, the surface of the prosthesis can include one or more reservoirs or cavities formed therein, as described further below.

The prosthesis can be fabricated utilizing any number of methods known in the art. For example, the prosthesis can be fabricated from a hollow or formed tube that is machined using lasers, electric discharge milling, chemical etching or other known techniques. Alternatively, the prosthesis can be fabricated from a sheet that is rolled into a tubular member, or formed of a wire or filament construction as known in the art.

The balloon can be in an expanded or unexpanded state during the loading of beneficial agent. Additionally, the balloon can be in a rolled or unrolled state during the loading of beneficial agent. The underlying structure of the balloon can be virtually any structural design and the balloon can be composed of any suitable material such as, but not limited to, polyester, pTFE (Teflon), nylon, Dacron, or combinations thereof. "Teflon" and "Dacron" are understood to be trade names for polymers available from DuPont Co., Wilmington, Del. In some embodiments, the surface of the balloon can include one or more reservoirs or cavities formed therein or ports for solution delivery.

The balloon can be fabricated utilizing any number of methods known in the art. For example, the balloon can be fabricated from a hollow or formed tube that is cover with thin membranes of polymer that is solution or physically (by laser or ultrasonically) welded to the tube. The inner volume of the balloon is then in direct contact with the tube such that air or aqueous solutions can be injected into the space under pressure to expand the balloon into any predefined shape that is of use. The surface of the balloon can be rolled to reduce the outer diameter of the final catheter balloon assemble.

The balloons can be loaded with a beneficial agent from a dilute solution of the agent made in an appropriate solvent (for example Ethanol) (if desired this solution could also contain multiple beneficial agents) and allowed to dry before the stent is crimped onto it. Alternatively, the coating could not be allowed to dry or cure past a "tacky" state before the stent is crimped onto it. This would enable the adhesion of the beneficial agent coating on the balloon to the inside of the prosthesis. This process increases the retention of the prosthesis onto the balloon (acting as a prosthesis retention enhancer) thus reducing the chance that the stent will move on the angioplasty balloon during the torturous trip to the coronary arteries. To prevent the film on the balloon from drying to quickly (i.e. becoming hard before the stent was placed over the balloon) the solution can contain a second liquid that has a higher boiling point (preferable water) and thus a slower drying time than the main solvent. Additionally, the use of a two solvent system (i.e. Ethanol-water) would allow the solvent to be adjusted such that the balloons beneficial agent (for example dexamethasone) is soluble enough to be laid down but the beneficial agent (for example ABT-578, rapamycin, and rapamycin analogies) on the prosthesis is not soluble enough to leach out of the prosthesis into the balloon coating or out of the balloon coating into the prosthesis coating during the drying time. Additionally, polymer barriers, timing layers, top or capcoats, especially on the luminal side of the prosthesis, or the use of bare metal interfaces can be used to prevent drug transfer from the balloon surface into the delivery polymer of the prosthesis. Alternately, some of the beneficial agent from the balloon could be allowed to transfer to the stent creating a gradient of the two beneficial agents released from the stent into the tissue. The binder can be composed of complex sugars (mannitol), starches (e.g., cellulose), collagens. In general the binder would be noncrystalline, have low water solubility, have good film forming characteristics, good solubility with solvents that may be used to dissolve the drug, biocompatible, inert (nonreactive with respect to the drug and also body tissues, fluids, etc), polymer, (e.g., hydrogel), can be hydrophobic if not hydrogel, especially if it is not permanently attached to balloon (if permanently attached, then can use hydrogel, can be used to absorb drug and then when balloon inflated, will squeeze out the drug into ablumenal tissue), low blood solubility if not permanently attached to balloon The prosthesis, balloon combination can be fabricated utilizing any number of methods known in the art. For example, the prosthesis can be slipped over the end of the balloon and aligned at the center of the balloon. The prosthesis can pre reduced in diameter such that as it is slipped over the end of the balloon there is a tight fit between the prosthesis and the balloon surface. Additionally, the prosthesis can be crimped onto the balloon to ensure that the prosthesis does not move during delivery of the prosthesis. The envisioned steps for this process would be: Dip or spray coat the balloon with the balloons beneficial agent, place the previously beneficial agent coated prosthesis onto a dry or tacky balloon and place Balloon/Stent into crimper and crimping.

As noted above, the prosthesis and the balloon are at least partially loaded with beneficial agent (10a, 10b, 10c). "Beneficial agent" as used herein, refers to any compound, mixture of compounds, or composition of matter consisting of a compound, which produces a beneficial or useful result. The beneficial agent can be a polymer, a marker, such as a radiopaque dye or particles, or can be a drug, including pharmaceutical and beneficial agents, or an agent including inorganic or organic drugs without limitation. The agent or drug can be in various forms such as uncharged molecules, components of molecular complexes, pharmacologically-acceptable salts such as hydrochloride, hydrobromide, sulfate, laurate, palmitate, phosphate, nitrate, borate, acetate, maleate, tartrate, oleate, and salicylate.

An agent or drug that is water insoluble can be used in a form that is a water-soluble derivative thereof to effectively serve as a solute, and on its release from the device, is converted by enzymes, hydrolyzed by body pH, or metabolic processes to a biologically active form. Additionally, the agents or drug formulations can have various known forms such as solutions, dispersions, pastes, particles, granules, emulsions, suspensions and powders. The drug or agent may or may not be mixed with polymer or a solvent as desired.

For purposes of illustration and not limitation, the drug or agent can include antithrombotics, anticoagulants, antiplatelet agents, thrombolytics, lipid-lowering agents, antiproliferatives, anti-inflammatories, agents that inhibit hyperplasia, inhibitors of smooth muscle cell proliferation, antibiotics, growth factor inhibitors, cell adhesion promoters, or cell adhesion inhibitors. Other drugs or agents include but are not limited to antineoplastics, antimitotics, antifibrins, antioxidants, agents that promote endothelial cell recovery, antiallergic substances, radiopaque agents, viral vectors, antisense compounds, oligionucleotides, cell permeation enhancers, angiogenesis agents, and combinations thereof.

Examples of such antithrombotics, anticoagulants, antiplatelet agents, and thrombolytics include unfractionated heparin, low molecular weight heparins, such as dalteparin, enoxaparin, nadroparin, reviparin, ardoparin and certaparin, heparinoids, hirudin, argatroban, forskolin, vapriprost, prostacyclin and prostacylin analogues, dextran, D-phe-pro-arg-chloromethylketone (synthetic antithrombin), dipyridamole, glycoprotein IIb/IIIa (platelet membrane receptor antagonist antibody), recombinant hirudin, and thrombin inhibitors such as Angiomax™, from Biogen, Inc., Cambridge, Mass.; and thrombolytic agents, such as urokinase, e.g., Abbokinase™ from Abbott Laboratories Inc., North Chicago, Ill., recombinant urokinase and pro-urokinase from Abbott Laboratories Inc., tissue plasminogen activator (Alteplase™ from Genentech, South San Francisco, Calif. and tenecteplase (TNK-tPA).

Examples of such cytostatic or antiproliferative agents include rapamycin and its analogs such as ABT-578, i.e., 3S,6R,7E,9R,10R,12R,14S,15E,17E,19E,21S,23S,26R,27R,34aS)-9,10,12,13,14,21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H pyrido[2,1-c][1,4]oxaazacyclohentriacontine-1,5,11,28,29(4H,6H,31H)-pentone, everolimus, tacrolimus and pimecrolimus, angiopeptin, angiotensin converting enzyme inhibitors such as captopril, e.g, Capoten® and Capozide® from Bristol-Myers Squibb Co., Stamford, Conn., cilazapril or lisinopril, e.g., Prinivil® and Prinzide® from Merck & Co., Inc., Whitehouse Station, N.J.; calcium channel blockers such as nifedipine, amlodipine, cilnidipine, lercanidipine, benidipine, trifluperazine, diltiazem and verapamil, fibroblast growth factor antagonists, fish oil (omega 3-fatty acid), histamine antagonists, lovastatin, e.g. Mevacor® from Merck & Co., Inc., Whitehouse Station, N.J. In addition, topoisomerase inhibitors such as etoposide and topotecan, as well as antiestrogens such as tamoxifen may be used.

Examples of such anti-inflammatories include colchicine and glucocorticoids such as betamethasone, cortisone, dexamethasone, budesonide, prednisolone, methylprednisolone and hydrocortisone. Non-steroidal anti-inflammatory agents include flurbiprofen, ibuprofen, ketoprofen, fenoprofen, naproxen, diclofenac, diflunisal, acetominophen, indomethacin, sulindac, etodolac, diclofenac, ketorolac, meclofenamic acid, piroxicam and phenylbutazone.

Examples of such antineoplastics include alkylating agents such as altretamine, bendamucine, carboplatin, carmustine, cisplatin, cyclophosphamide, fotemustine, ifosfamide, lomustine, nimustine, prednimustine, and treosulfin, antimitotics such as vincristine, vinblastine, paclitaxel, e.g., TAXOL® by Bristol-Myers Squibb Co., Stamford, Conn., docetaxel, e.g., Taxotere® from Aventis S. A., Frankfort, Germany, antimetabolites such as methotrexate, mercaptopurine, pentostatin, trimetrexate, gemcitabine, azathioprine, and fluorouracil, and antibiotics such as doxorubicin hydrochloride, e.g., Adriamycin® from Pharmacia & Upjohn, Peapack, N.J., and mitomycin, e.g., Mutamycin® from Bristol-Myers Squibb Co., Stamford, Conn., agents that promote endothelial cell recovery such as Estradiol Additional drugs which may be utilized in this application include inhibitors of tyrosine kinase such as RPR-101511A, PPAR-alpha agonists such as Tricor™ (fenofibrate) from Abbott Laboratories Inc., North Chicago, Ill., PPAR-gamma agonists selected from a group consisting of rosiglitazaone (Glaxo Smith Kline) and Pioglitazone (Takeda), HMG CoA reductase inhibitors selected from a group consisting of lovastatin, atorvastatin, simvastatin, pravastatin, cerivastatin and fluvastatin, endothelin receptor antagonists such as ABT-627 having general formula $C_{29}H_{38}N_2O_6 \cdot ClH$, and the following structural formula

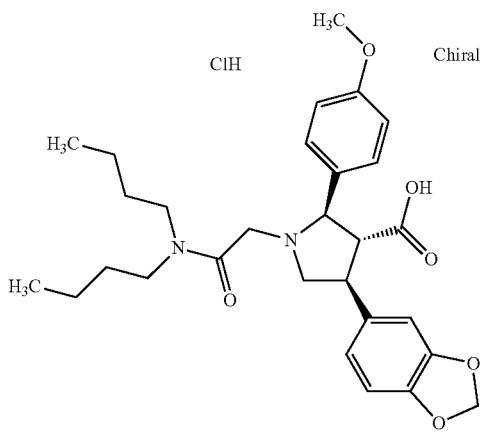

from Abbott Laboratories Inc., North Chicago, Ill.; matrix metalloproteinase inhibitors such as ABT-518 having general formula $C_{21}H_{22}F_3NO_8S$ and having the following structural formula

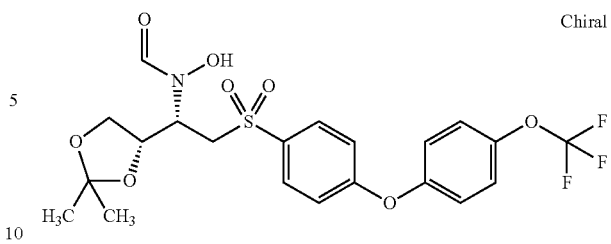

from Abbott Laboratories Inc., North Chicago, Ill., antiallergic agents such as permirolast potassium nitroprusside, phosphodiesterase inhibitors, prostaglandin inhibitors, suramin, serotonin blockers, steroids, thioprotease inhibitors, triazolopyrimidine, and nitric oxide.

While the foregoing beneficial agents are known for their preventive and treatment properties, the substances or agents are provided by way of example and are not meant to be limiting. Further, other beneficial agents that are currently available or may be developed are equally applicable for use with the present invention.

If desired or necessary, the beneficial agent can include a binder to carry, load, or allow sustained release of an agent, such as but not limited to a suitable polymer or similar carrier. The term "polymer" is intended to include a product of a polymerization reaction inclusive of homopolymers, copolymers, terpolymers, etc., whether natural or synthetic, including random, alternating, block, graft, branched, cross-linked, blends, compositions of blends and variations thereof. The polymer may be in true solution, saturated, or suspended as particles or supersaturated in the beneficial agent. The polymer can be biocompatible, or biodegradable.

For purpose of illustration and not limitation, the polymeric material include phosphorylcholine linked macromolecules, such as a macromolecule containing pendant phosphorylcholine groups such as poly($MPC_w$:$LMA_x$:$HPMA_y$:$TSMA_z$), where MPC is 2-methacryoyloxyethylphosphorylcholine, LMA is lauryl methacrylate, HPMA is hydroxypropyl methacrylate and TSMA is trimethoxysilylpropyl methacrylate, polycaprolactone, poly-D,L-lactic acid, poly-L-lactic acid, poly(lactide-co-glycolide), poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), cyanoacrylates, poly(trimethylene carbonate), poly(iminocarbonate), polyalkylene oxalates, polyphosphazenes, polyiminocarbonates, and aliphatic polycarbonates, fibrin, fibrinogen, cellulose, starch, collagen, Parylene®, Parylast®, polyurethane including polycarbonate urethanes, polyethylene, polyethylene terephthalate, ethylene vinyl acetate, ethylene vinyl alcohol, silicone including polysiloxanes and substituted polysiloxanes, polyethylene oxide, polybutylene terephthalate-co-PEG, PCL-co-PEG, PLA-co-PEG, polyacrylates, polyvinyl pyrrolidone, polyacrylamide, and combinations thereof. Non-limiting examples of other suitable polymers include thermoplastic elastomers in general, polyolefin elastomers, EPDM rubbers and polyamide elastomers, and biostable plastic material such as acrylic polymers, and its derivatives, nylon, polyesters and epoxies. Preferably, the polymer contains pendant phosphoryl groups as disclosed in U.S. Pat. Nos. 5,705, 583 and 6,090,901 to Bowers et al. and U.S. Pat. No. 6,083, 257 to Taylor et al., which are all incorporated herein by reference.

The beneficial agent can include a solvent. The solvent can be any single solvent or a combination of solvents. For purpose of illustration and not limitation, examples of suitable solvents include water, aliphatic hydrocarbons, aromatic hydrocarbons, alcohols, ketones, dimethyl sulfoxide, tetrahydrofuran, dihydrofuran, dimethylacetamide, acetates, and combinations thereof. Preferably, the solvent is ethanol. More preferably, the solvent is isobutanol. Additionally, in another aspect of the invention, multiple beneficial agents are dissolved or dispersed in the same solvent. For purpose of illustration and not for limitation, dexamethasone, estradiol, and paclitaxel are dissolved in isobutanol. Alternatively, dexamethasone, estradiol, and paclitaxel are dissolved in ethanol. In yet another example, dexamethasone, estradiol, and ABT-578, i.e., the rapamycin analog, 3S,6R,7E,9R,10R,12R,14S,15E,17E,19E,21S,23S,26R,27R,34aS)9,10,12,13,14,21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone; 23,27-Epoxy-3H-pyrido[2,1-c][1,4]oxaazacyclohentriacontine-1,5,11,28,29(4H,6H,31H)-pentone, are dissolved together in one solvent. Preferably, the solvent is ethanol. More preferably, the solvent is isobutanol.

Additionally, the beneficial agent includes any of the aforementioned drugs, agents, polymers, and solvents either alone or in combination.

A number of methods can be used to load the beneficial agent onto the surface of the prosthesis or balloon to provide for a controlled local areal density of beneficial agent. For example, the prosthesis or balloon can be constructed to include pores or reservoirs which are impregnated or filled with beneficial agent or multiple beneficial agents. The pores can be sized or spaced apart to correspond to or limit the amount of beneficial agent contained therein in accordance with the desired local areal density pattern along the length of the interventional device, wherein larger pores or more dense spacing would be provided in such portions intended to have a greater local areal density. Alternatively, uniform pores sizes can be provided but the amount of beneficial agent loaded therein is limited accordingly. Additionally, if desired, a membrane of biocompatible material can then be applied over the pores or reservoirs for sustained or controlled release of the beneficial agent from the pores or reservoirs.

According to some of the embodiments, the beneficial agent can be loaded directly onto the prosthesis or balloon or alternatively, the beneficial agent is loaded onto a base material layer that is applied to a surface of the prosthesis or balloon. For example and not limitation, a base coating, such as a binder or suitable polymer, is applied to a selected surface of the prosthesis or balloon such that a desired pattern is formed on the prosthesis or balloon surface. Beneficial agent is then applied directly to the pattern of the base material.

In one aspect of the invention, the desired pattern corresponds to the desired controlled local areal density. For example, a greater amount of base material layer is applied to portions of the prosthesis or balloon intended to have a greater local areal density of beneficial agent, and a lesser amount of base material is applied to portions of the prosthesis or balloon intended to have a lower local areal density of beneficial agent.

Alternatively, a suitable base coating capable of retaining beneficial agent therein can be applied uniformly over the surface of the prosthesis or balloon, and then selected portions of the base coating can be loaded with the beneficial agent in accordance with the invention. A greater amount of beneficial agent would be loaded over a unit surface area of the base coating intended to have a greater local areal density and a lower amount of beneficial agent would be loaded over a unit surface area intended to have a lower local areal density.

In yet another embodiment of the present invention, the beneficial agent can be applied directly to the surface of the prosthesis or balloon. Generally a binder or similar component can be required to ensure sufficient adhesion. For example, this coating technique can include admixing the beneficial agent with a suitable binder or polymer to form a coating mixture, which is then coated onto the surface of the prosthesis or balloon. The coating mixture is prepared in higher or lower concentrations of beneficial agent as desired, and then applied to selected portions of the prosthesis or balloon appropriately. In general the binder used with the beneficial agent for the prosthesis may be difference then the binder used for the beneficial agent for the balloon.

In any of the embodiments disclosed herein, a porous or biodegradable membrane or layer made of biocompatible material can be coated over the beneficial agent for sustained release thereof, if desired.

Conventional coating techniques can be utilized to coat the beneficial agent onto the surface of the prosthesis or balloon such as spraying, dipping or sputtering and still provide the desired effect if performed appropriately. With such techniques, it may be desirable or necessary to use known masking or extraction techniques to control the location and amount in which beneficial agent is loaded. Although not required, prior to coating the prosthesis or balloon with beneficial agent, optical machine vision inspection of the prosthesis or balloon may be utilized to ensure that no mechanical defects exist. Defective prostheses or balloons may be rejected before wasting beneficial agent, some of which may be very costly.

In accordance with one aspect of the invention, a method of loading beneficial agent onto a prosthesis for delivery within a lumen is disclosed. The method comprises the steps of providing a prosthesis, beneficial agent to be delivered from the prosthesis, and a fluid-dispenser having a dispensing element capable of dispensing the beneficial agent in discrete droplets, wherein each droplet has a controlled trajectory. The method further includes creating relative movement between the dispensing element and the prosthesis to define a dispensing path and selectively dispensing the beneficial agent in a raster format to a predetermined portion of the prosthesis along the dispensing path. In particular, the beneficial agent is selectively dispensed from the dispensing element to a predetermined portion of the prosthesis in a raster format along a dispensing path. As used herein "raster format" refers to a continuous or non-continuous dispensing pattern of droplets of beneficial agent.

According to another aspect of the invention, the method of loading beneficial agent onto the prosthesis includes providing a prosthesis including a tubular member having a central axis defined along a length of the tubular member. This method further includes dispensing beneficial agent In accordance with another aspect of the invention, additional beneficial agents or multiple beneficial agents can be loaded onto the prosthesis as described above. Therefore, further in accordance with the invention, an interventional device comprising a prosthesis loaded with a beneficial agent and additional beneficial agents is provided.

Particularly, the method described in detail above for one beneficial agent can be modified to allow for loading multiple beneficial agents onto a prosthesis and/or a balloon, which might ordinarily lead to undesirable results when using conventional loading techniques. For example and not limitation, the first beneficial agent and the second beneficial agent may have different physical and/or chemical characteristics preventing the beneficial agents from being capable of dissolving in the same solvent, or at the same pH or temperature. In particular, the first beneficial agent can be dissolved in a solvent that is immiscible with the solvent in which the second beneficial agent is dissolved. Alternatively, the first beneficial agent and the second beneficial agent may be incompatible with each other. In particular, the first beneficial agent and the second beneficial agent can be undesirably chemically reactive or may have undesirably different release rates (or contrarily, undesirably similar release rates). Additionally, the first and second beneficial agents can simply be detrimental to each other, e.g., one of the beneficial agents may degrade the efficacy of the other beneficial agent. Thus, although loading the particular multiple beneficial agents onto the same surface of a prosthesis or balloon can be desired it often may be problematic due to some incompatibility when using a conventional loading technique. In accordance with the present invention, a method of loading such beneficial agents and an interventional device that combine a prosthesis and a balloon for the delivery of such beneficial agents is provided.

As noted above, the beneficial agent can include a drug and polymer mixture. In accordance with the method of the invention, the first and second beneficial agents can correspond to drug-polymer mixtures having different concentrations of polymer to effect different release rates of the particular drug in each beneficial agent. For example, the drug-polymer mixture having a higher concentration of polymer would have a slower release of the drug within the lumen than a drug-polymer mixture having a lower concentration. Alternatively, rather than providing drug-polymer mixtures having different polymer concentrations to provide different release rates, it is also possible to dispense beneficial agents using different polymers or other binders, wherein the specific polymer or binder has different diffusivity or affinity to assure delivery of the beneficial agents at different rates. Thus, in accordance with the invention, multiple beneficial agents can be released at rates appropriate for their activities, such that the prosthesis-balloon combination of the invention has multiple beneficial agents which elute off the prosthesis-balloon combination at desired rates.

For example, a cationic phosphorylcholine-linked polymer which has a higher affinity for anionic beneficial agents can be blended and dispersed as a first beneficial agent and lipophilic phosphorylcholine-linked polymer can be blended with lipophilic drugs as the second beneficial agent to effect different release rates respectively.

In yet another embodiment of the invention, one of the first and second beneficial agents loaded onto the prosthesis-balloon combination may be more hydrophobic than the other. Thus, in accordance with the invention is provided a prosthesis-balloon combination including first and second beneficial agents wherein one of the beneficial agents is more hydrophobic than the other. In this manner, the less hydrophobic beneficial agent is separated from the more hydrophobic beneficial agent, thereby not modifying the release rate of the more hydrophobic beneficial agent. For example and not limitation, the less hydrophobic beneficial agent may be ABT 620 {1-Methyl-N-(3,4,5-trimethoxyphenyl)-1H-indole-5-sulfonamide}, which is disclosed in U.S. Pat. No. 6,521,658, the disclosure of which is incorporated herein by reference; ABT 627, which is disclosed in U.S. Pat. No. 5,767,144, the disclosure of which is incorporated herein by reference; ABT 518 {[S—(R*,R*)]—N-[1-(2,2-dimethyl-1,3-dioxol-4-yl)-2-[[4-[4-(trifluoro-methoxy)-phenoxy]phenyl]sulfonyl] ethyl]-N-hydroxyformamide}, which is disclosed in U.S. Pat. No. 6,235,786, the disclosure of which is incorporated herein by reference; dexamethasone, and the like and the more hydrophobic beneficial agent may be Fenofibrate, Tricor™ or the rapamycin analog, ABT-578, i.e., 3S,6R,7E,9R,10R,12R, 14S,15E,17E,19E,21S,23S,26R,27R,34aS)-9,10,12,13,14, 21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14, 20,26-hexamethyl-23,27-epoxy-3H-pyrido[2,1-c][1,4] oxaazacyclohentriacontine-1,5,11,28,29(4H,6H,31H)-pentone; 23,27-Epoxy-3H-pyrido[2,1-c][1,4]oxaazacyclo-hentriacontine-1,5,11,28,29(4H,6H,31H)-pentone, which is disclosed in U.S. Pat. No. 6,015,815, U.S. Pat. No. 6,329,386, WO 02/123505, and WO 03/129215, disclosures of which are incorporated herein by reference thereto.

Figure 5A:
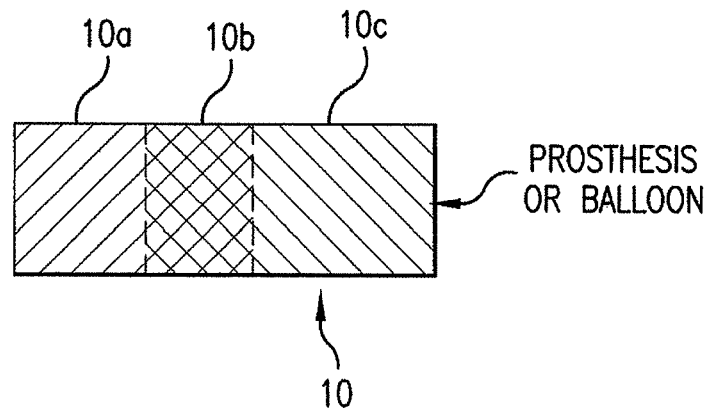
FIG. 5a-c is a schematic representation of a prosthesis or balloon loaded with beneficial agent having a first portion and a second portion having different local areal densities of beneficial agent in accordance with the present invention, and graph depicting corresponding areal density.
Figure 5B:
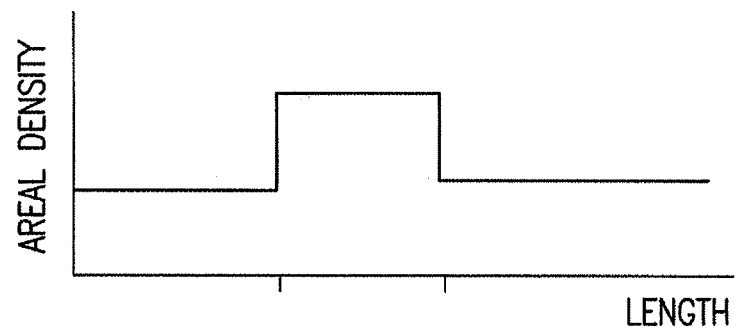
Figure 5C:
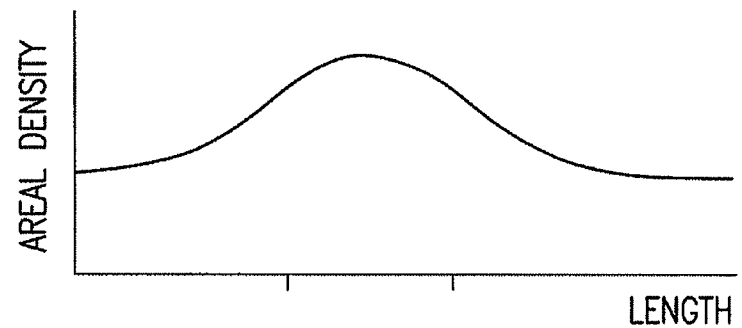

Further in accordance with the invention, using the method and systems described above, a first beneficial agent loaded onto the prosthesis can have a first local areal density and a second beneficial agent loaded onto the balloon can have a second local areal density. As used herein, "areal density" refers to the amount of beneficial agent per unit surface area of a selected portion of the prosthesis or balloon. "Local areal density" refers to the dosage of beneficial agent per local surface area of the prosthesis or balloon. The local areal density of the first beneficial agent and the local areal density of the second beneficial agent can be uniform across each respective portion to define stepped changes in local area density as depicted in FIG. 5b or can be varied across a selected portion of the prosthesis or balloon to define gradients of local area density, as depicted in FIG. 5c. Accordingly, an interventional device is provided having a prosthesis or balloon that is at least partially loaded with beneficial agent having a local areal density that is varied along a selected portion of the body of the prosthesis or balloon.

In another embodiment of the invention, the local areal density is varied as a continuous gradient along a selected portion of the prosthesis or balloon as shown in FIG. 5c. Accordingly, in one aspect of the invention the local areal density of beneficial agent is varied such as to provide a prosthesis or balloon having a local areal density of beneficial agent at the ends of the prosthesis or balloon that is different than the local areal density of beneficial agent at an intermediate section of the prosthesis or balloon. For purpose of illustration and not limitation, the local areal density of beneficial agent at the intermediate section of the prosthesis can be greater than that at the proximal and distal ends of the prosthesis as shown in FIG. 5c. Alternatively, the proximal and distal ends of the prosthesis can have a greater local areal density of beneficial agent than that on the intermediate section of the prosthesis. In a preferred embodiment of the invention, the varied local areal density of beneficial agent corresponds to the location of a lesion when the prosthesis is deployed within a lumen. For example, the prosthesis or balloon can be loaded to have a greater local areal density of beneficial agent along a preselected portion of the prosthesis or balloon that corresponds to the location of the lesion when the prosthesis is deployed in a lumen. Thus, targeted therapy may be achieved with the interventional device of the present invention.

As noted above, the beneficial agent is at least partially loaded onto a surface of the prosthesis. Further in accordance with the invention the prosthesis includes a first surface and a second surface that are at least partially loaded with beneficial agent. In one embodiment of the invention, the first surface and the second surface each correspond to one of the inner surface and the outer surface of the prosthesis. Thus, according to this particular embodiment, beneficial agent, as defined above, is loaded onto the inner or luminal surface of a prosthesis as well as the outer surface of the prosthesis. In this aspect of the invention, the interventional device can be designed to provide combination therapy of beneficial agents to targeted locations. For example and not limitation, the particular beneficial agent loaded on the balloon can be intended for systemic or down stream release, whereas the particular beneficial agent loaded onto the surface of the prosthesis is intended for release into the wall of the vessel. In accordance with one aspect of the invention, the beneficial agents loaded onto the balloon include, without limitation, antiplatelet agents, aspirin, cell adhesion promoters, agents that promote endothelial recovery, agents that promote migration, estradiol, anti-inflammatories, anti-proliferatives, smooth muscle inhibitors, cell adhesion promoters, and the rapamycin analog ABT-578, i.e., 3S,6R,7E,9R,10R,12R, 14S,15E,17E,19E,21S,23S,26R,27R,34aS)-9,10,12,13,14, 21,22,23,24,25,26,27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14, 20,26-hexamethyl-23,27-epoxy-3H-pyrido[2,1-c][1,4] oxaazacyclohentriacontine-1,5,11,28,29(4H,6H,31H)-pentone; 23,27-Epoxy-3H-pyrido[2,1-c][1,4] oxaazacyclohentriacontine-1,5,11,28,29(4H,6H,31H)-pentone. The beneficial agents loaded onto the prosthesis include without limitation, antiplatelet agents, aspirin, cell adhesion promoters, agents that promote endothelial recovery, agents that promote migration, estradiol, anti-inflammatories, anti-proliferatives, smooth muscle inhibitors, cell adhesion promoters, angiotensin II receptor antagonists such as losartan, eposartan, valsartan and candesartan, antihypertensive agents such as carvedilol, and the rapamycin analog ABT-578, i.e., 3S,6R,7E,9R,10R,12R,14S,15E,17E,19E, 21S,23S,26R,27R,34aS)-9,10,12,13,14,21,22,23,24,25,26, 27,32,33,34,34a-Hexadecahydro-9,27-dihydroxy-3-[(1R)-2-[(1S,3R,4R)-3-methoxy-4-tetrazol-1-yl)cyclohexyl]-1-methylethyl]-10,21-dimethoxy-6,8,12,14,20,26-hexamethyl-23,27-epoxy-3H-pyrido[2,1-c][1,4] oxaazacyclohentriacontine-1,5,11,28,29(4H,6H,31H)-pentone; 23,27-Epoxy-3H-pyrido[2,1-c][1,4] oxaazacyclohentriacontine-1,5,11,28,29(4H,6H,31H)-pentone.

As noted above, the beneficial agent is loaded onto the prosthesis to provide a controlled local areal density across a length of the interventional device. That is, it may be desirable to provide a greater concentration of beneficial agent at one portion of a prosthesis and a lower concentration, or perhaps no beneficial agent, at another portion of the prosthesis. For example, in one preferred embodiment, a greater local areal density can be provided at a first portion, e.g., intermediate portion 10b, of a prosthesis or balloon 10, as shown in FIG. 5a, while providing a lower local areal density of beneficial agent to a second portion, e.g., one or both end portions (10a, 10c), of the prosthesis or balloon 10. In accordance with the present invention, each of the first and second portions of the prosthesis or balloon may be defined by any of a variety of patterns or selected portions of the prosthesis or balloon. For example, the first portion of the prosthesis can be defined by longitudinal connectors whereas the second portion of the prosthesis is defined by annular rings, or vice versa.

Alternatively, the beneficial agent distribution profile for the interventional device may be controlled to include any of a variety of desired patterns. For example, the prosthesis or balloon can have a decreased local areal density of beneficial agent on the distal and proximal ends, as noted above. This profile is highly desirable in preventing adverse dosing of beneficial agent if multiple prostheses are placed in combination with each other (for example overlapping prostheses or kissing prostheses at bifurcations) but still provides for decreased dosage of the extreme ends of the interventional device as a whole. Alternatively, as embodied herein, the beneficial agent distribution profile can provide a controlled local areal density that is uniform along the length of a first prosthesis and a second prosthesis in combination, or multiple prostheses in combination. Alternatively, in accordance with the invention, the beneficial agent distribution profile provides a controlled local areal density that is varied along the length of the first prosthesis and the second prosthesis in combination, or multiple prostheses in combination.

Another feature of the present invention includes applying a layer of base material on a selected portion of the prosthesis or balloon described above. The beneficial agent is loaded onto the base material layer according to the methods described above. The base material layer preferably defines a pattern for loading the beneficial agent onto the prosthesis or balloon.

The present invention also encompasses, for any of the embodiments disclosed, the application of a rate-controlling topcoat over the beneficial agent loaded prosthesis, balloon, or prosthesis-balloon combination for further controlling or sustaining the release of beneficial agent. The rate-controlling topcoat may be added by applying a coating layer posited over the beneficial agent loaded prosthesis, balloon, or prosthesis-balloon combination. The thickness of the layer is selected to provide such control. Preferably, the overcoat is applied by spray coating or fluid-jet technology. Advantageously, fluid jetting an overcoat such as a polymer overcoat allows thinner and more uniform layers. However other conventional methods can be used such as other fluid-dispensers, vapor deposition, plasma deposition, spraying, or dipping, or any other coating technique known in the art.

The present invention also encompasses, for any of the embodiments disclosed, the application of polymer barriers, timing layers, top or capcoats, especially on the luminal side of the prosthesis, or the use of bare metal interfaces to be used to prevent drug transfer from the balloon surface into the delivery polymer of the prosthesis. Alternately, some of the beneficial agent from the balloon could be allowed to transfer to the stent creating a gradient of the two beneficial agents released from the stent into the tissue.

The present invention also provides a method for manufacturing an interventional device for delivery of beneficial agents. This method comprises the steps of providing a prosthesis to be deployed within a lumen; providing a balloon configured to be deployed in an overlapping relationship with the prosthesis, the prosthesis and the balloon in combination defining at least an overlapping segment; and loading the prosthesis with a first beneficial agent and the balloon with a second beneficial agent to provide a controlled local areal density along a length of the prosthesis and the balloon in combination. The method described in detail above is preferred for such loading step.

The present invention also provides a method of delivering beneficial agents. In accordance with this method, as described in detail in conjunction with the description of the interventional device of the present invention above, the method comprising the steps of providing a prosthesis having a tubular body when deployed in a lumen; providing a balloon capable of expanding in the lumen; loading the prosthesis with a first beneficial agent and the balloon with a second beneficial agent; deploying the prosthesis into a lumen with the beneficial agent coated balloon deploying the beneficial agent coated prosthesis into the lumen to define in combination at least one overlapping segment; wherein the beneficial agents are loaded onto the prosthesis and the balloon to provide a controlled local areal density of beneficial agent across a length of the prosthesis when deployed. The method described in detail above is preferred for such loading step.

Figure 3:
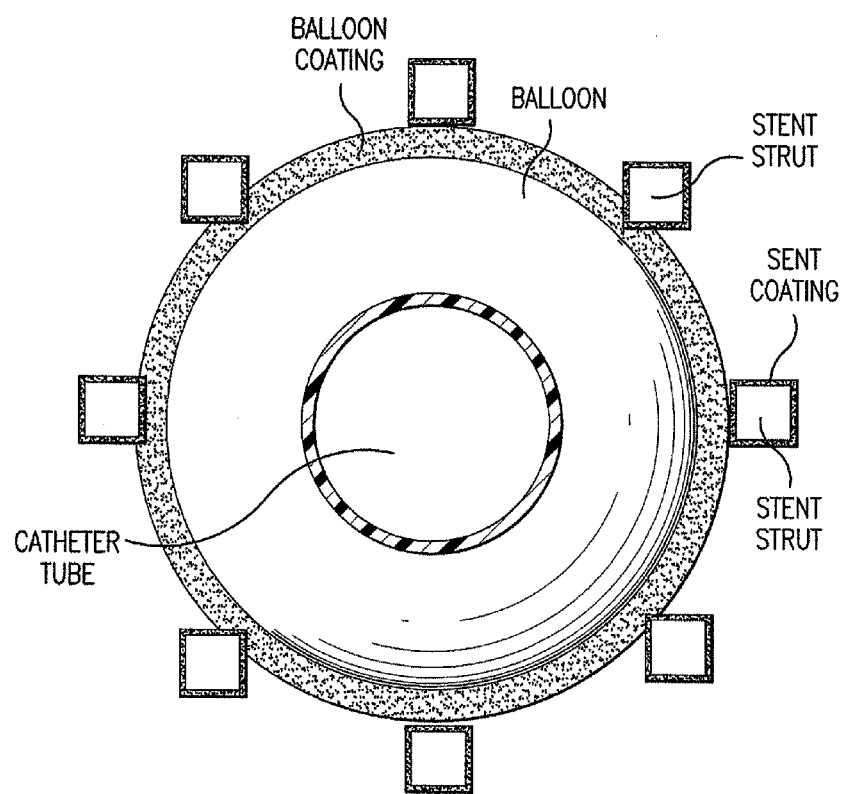
FIG. 3 is a schematic representation of an embodiment of the system of the present invention showing a cross section through a stent crimped onto a catheter balloon. The dark center is the catheter body, the white is the balloon, the squares are the individual struts of the stent, the shading on the balloon representing a coating of a second beneficial agent on the balloon and the shading of the stent struts representing a coating of a first beneficial agent on the stent.
Figure 4A:
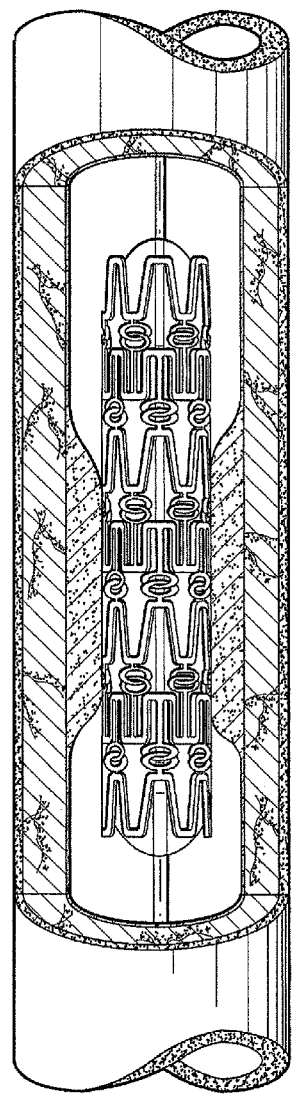
FIG. 4 is a schematic representation of the embodiment of the system of the present invention for the delivery of the beneficial agents to a vessel wall. The drawing shows the process of delivering a stent from a balloon to expand the lumen of a narrowed vessel. 4a. Shows the placement of the balloon-stent combination at the site of delivery. 4b. shows the expansion of the balloon, which results in the expansion of the stent against the vessel wall. 4c show the result after the balloon is deflated and removed leaving the stent behind.
Figure 4B:
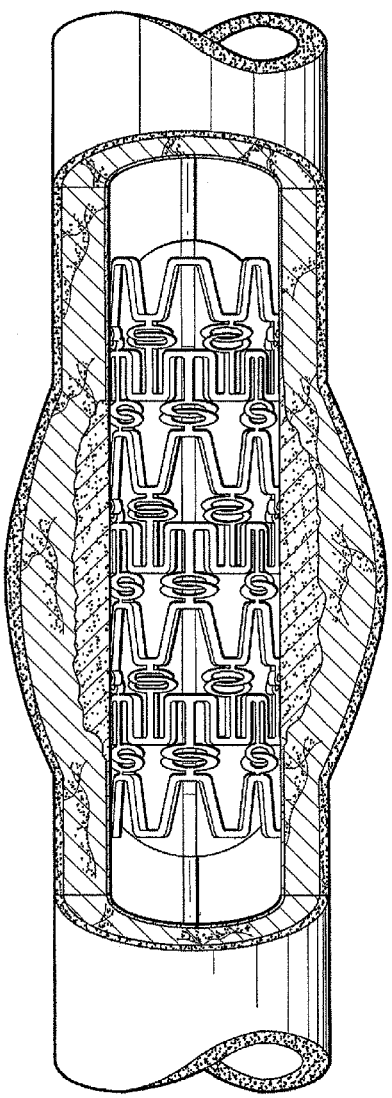
Figure 4C:
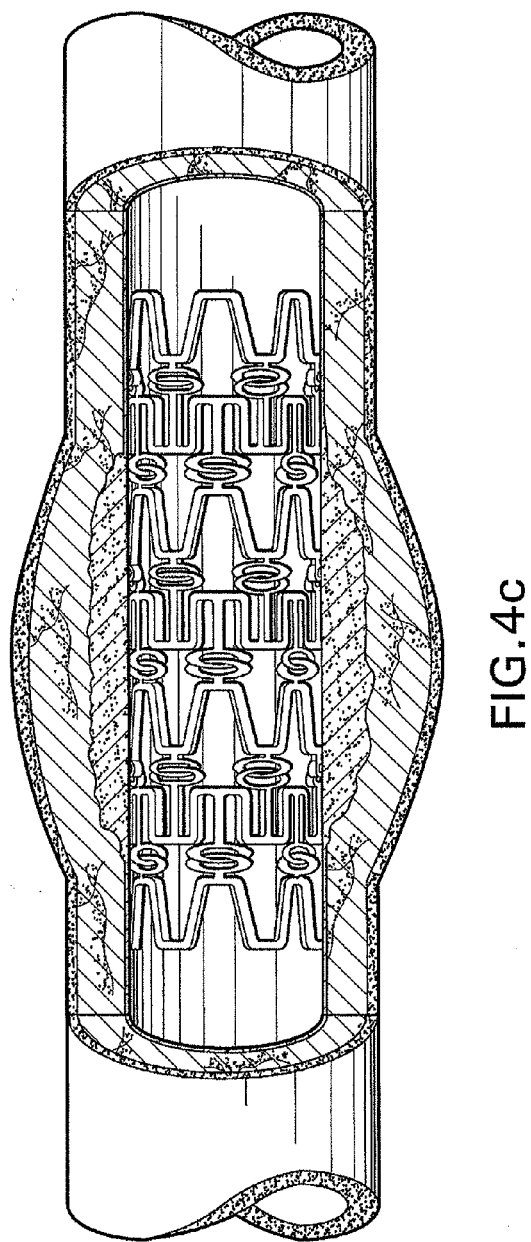

For purposes of explanation and illustration, and not limitation, an exemplary embodiment of the interventional device in accordance with the invention is shown schematically in FIGS. 2 and 3. In accordance with one aspect of the invention, as shown schematically in FIGS. 2 and 3, the interventional device generally includes a prosthesis loaded with beneficial agent (preferably ABT-578, rapamycin, or rapamycin analogies, alone or in combination with an additional drug such as dexamethasone or estradiol) to provide a local delivery of a first beneficial agent across a treatment zone and a balloon with a second beneficial agent (preferably paclitaxel, taxanes, or other taxane derivatives, alone or in combination with an additional drug) delivered a cross a second overlapping treatment zone. Alternatively, the a prosthesis could be loaded with beneficial agent (preferably paclitaxel, taxanes, or other taxane derivatives alone or in combination with an additional drug such as dexamethasone or estradiol) to provide a local delivery of a first beneficial agent across a treatment zone and a balloon with a second beneficial agent (preferably ABT-578, rapamycin, or rapamycin analogies, alone or in combination with an additional drug) delivered a cross a second overlapping treatment zone. Particularly, as embodied herein the prosthesis may be a stent, a graft or a stent-graft, as previously noted, for intravascular or coronary delivery and implantation. However, the prosthesis may be any type of implantable member capable of being loaded with beneficial agent. The balloon may be any type of catheter based expandable entity that can act to expand the prosthesis, the local tissue, or push the second beneficial agent against the lumen wall.

In an alternative embodiment, as shown schematically in FIGS. 6a and 6b, the balloon catheter does not have a prosthesis thereon. As illustrated in FIGS. 6a and 6b, the balloon surface is coated with a beneficial agent.

The present invention will be further understood by the examples set forth below, which are provided for purpose of illustration and not limitation.

The following examples demonstrate how various embodiments of the present invention may be practiced. By "simultaneous" it is meant that a coated prosthesis (e.g., stent) is mounted on a coated balloon and the stent and balloon are delivered to the desired location at the same time. By "independent", it is meant that the coated balloon is delivered either before or after the coated stent is delivered. By "combined", it is meant that beneficial agent(s) are delivered from both the balloon and the prosthesis to the vessel tissue."

EXAMPLES

Example 1

Loading of Stents with Beneficial Agents or Multiple Beneficial Agents

I. Coating the Stents with PC1036

Prior to any experimentation, coated stents are prepared. These are 3.0 mm×15 mm 316L electropolished stainless steel stents. Each stent is spray coated using a filtered 20-mg/mL solution of phosphorylcholine polymer PC1036 (product of Biocompatibles Ltd., Farnham, Surrey, UK) in ethanol. The stents are initially air dried and then cured at 70° C. for 16 hours. They are then sent for gamma irradiation at <25 KGy.

II. Loading the Stents with Drugs of Interest

In these experiments, beneficial agents are loaded onto stents and elution profiles examined. In general, the procedure is as follows. Multiple PC-coated stents are loaded with each of several drugs or combinations thereof from solution. The solutions of the drugs are usually in the range of 2-20 mg/mL of ABT-578 and 10.0 mg/mL dexamethasone in 100% ethanol, with ~10% PC1036 added to the solution to enhance film formation.

The stents are weighed before loading with the drug solution. To load approximately 10 µg/mL of each drug, a solution with equal amounts of ABT-578 and dexamethasone is sprayed onto the stent in a controlled fashion. The stent is allowed to dry before the stents are re-weighted to determine total drug load. The loaded, dry stents are stored in a refrigerator and are protected from light.

III. Extracting Drugs from the Stents

For each drug, 3 stents are used to evaluate the total amount of drug loaded by the above procedure. The stents are immersed in 6 mL of 50% ethanol, 50% water solution and sonicated for 20 minutes. The concentration of the drug in the extraction solution is analyzed by HPLC.

Example 2

Loading of Balloons with Beneficial Agents or Multiple Beneficial Agents

I. Preparing the Balloon for Drug Loading

Multiple balloons (Jomed 15 mm×3.0 mm) are rolled to minimize the final catheter crossing profile. If needed the balloons where washed in ethanol.

II. Loading the Balloon with Drugs of Interest

In these experiments, beneficial agents are loaded onto balloons. In general, the procedure is as follows. Multiple balloons (Jomed 15 mm×3.0 mm) are loaded with paclitaxel from a solution. The solutions of paclitaxel are usually in the range of 2-20 mg/mL of paclitaxel in 100% ethanol.

The balloons are weighed before loading with the drug solution. To load approximately 200 to 600 ug of paclitaxel, the balloons are dipped into a solution of paclitaxel. The balloon is removed in a controlled fashion to control drying. The stent is allowed to dry before the balloons are re-weighed to determine total drug load. The loaded, dry balloons are stored at room temperature and are protected from light.

III. Extracting Drugs from the Balloon

For each drug, 3 balloons are used to evaluate the total amount of drug loaded by the above procedure. The balloons are expanded and immersed in 6 mL of 50% ethanol, 50% water solution and sonicated for 20 minutes. The concentration of the drug in the extraction solution is analyzed by HPLC.

Example 3

Crimping of Beneficial Agent-Coated Stents onto Beneficial Agent-Coated Balloons Multiple stents loaded with ABT-578 and top coated with PC1036 are placed over the end of catheter balloons which have been coated with paclitaxel. The stent is centered over the radiopaque markers of the balloon and crimped onto the balloon using a Machine Solutions drug eluting stent crimper. The stent-balloon final product is then leak-tested and visually inspected to ensure the quality of the final product. The catheter assembly is then packaged in Tyvek pouches, labeled, and ETO sterilized.

Example 4

Simultaneous Combined Delivery of a First Beneficial Agent on Prosthesis and a Second Beneficial Agent on Balloon This example describes delivery of a stent containing at least one beneficial agent using a balloon coated with a second beneficial agent(s). In this example, a prosthesis will be coated with at least one beneficial agent and will be mounted on an angioplasty balloon, which has been coated with a second beneficial agent(s). This complete system will be inserted into the body via a peripheral vessel, and advanced to the lesion targeted for treatment. After location at the lesion site, the angioplasty balloon containing the second beneficial agent(s) will be expanded, simultaneously delivering said beneficial agent(s) as well as deploying the prosthesis containing the first beneficial agent(s). The simultaneous delivery will use a technique often described as direct stenting, in which no pre-dilatation of the vessel at the site of the lesion is involved and the delivery of each beneficial agent begins during the same time period. Alternatively, the simultaneous delivery can be completed after pre-dilatation with an uncoated balloon or with a coated balloon. When deployment of the prosthesis is complete, the balloon will be deflated and removed from the body, leaving the prosthetic device in place to continue delivering the first beneficial agent(s) over time. Beneficial agents on the prosthesis or the balloon can be the same or different.

Example 5

Independent Combined Delivery of First Beneficial Agent(s) on Prosthesis and Second Beneficial Agent(s) on Balloon A balloon coated with one or more beneficial agents, but containing no prosthesis, will be inserted into the body, and advanced to the lesion site where it will be dilated to expand the vessel. This technique is commonly described as pre-dilatation. Delivery of a second beneficial agent(s) to the lesion site will proceed upon expansion of this balloon. The balloon will then be deflated and removed from the body. At that time, a second intervention, in which a second balloon without a beneficial agent, containing a prosthesis coated with one or more beneficial agents, will be introduced via the peripheral vessel. Upon expansion of the second balloon at the pre-dilated lesion site, the prosthesis will be expanded and will begin to deliver one or more beneficial agents to the lesion. The second balloon will then be removed from the body.

Example 6

Independent Combined Delivery of First Beneficial Agent(s) on Prosthesis with a Post-Expansion Delivery of a Second Beneficial Agent(s) from a Balloon This procedure involves the delivery of a prosthesis containing a first beneficial agent(s), using a balloon that has no beneficial agent. In this case, the balloon catheter, containing a drug-loaded prosthesis, is advanced to the lesion site, and expanded to deliver the device and initiate the delivery of the beneficial agent(s). The balloon is then deflated and removed from the body. At this time, a second balloon, coated with a second beneficial agent(s), is inserted into the peripheral vessel and advanced to the lesion site. A second balloon expansion is then conducted to further expand the previously placed stent or to deliver a second beneficial agent or agents to the site of the lesion. Beneficial agents on the prosthesis or the balloon can be the same or different.

Example 7

Delivery of a Second Beneficial Agent on Balloon to Treat In-Stent Restenosis This intervention involves the dilation of a vessel with a balloon that is coated with a second beneficial agent(s) at a restenosed lesion site where a stent or stents have been previously placed. In this way, restenosis of a vessel in which an intervention has previously failed can be adequately treated without placement of an additional prosthesis or prosthesis at the same site.

Comparative Studies

This study compared the effects of Zotarolimus coated angioplasty balloons and Zotarolimus coated stents on the reduction of formation of neointima commonly associated with restenosis. Also evaluated was the influence of Zotarolimus delivered to one coronary artery from a balloon or stent to neotintimal hyperplasia in a separate coronary artery implanted with a bare metal stent. The results of this study indicate the delivery of beneficial agent directly from an angioplasty balloon is an attractive alternative to a drug eluting stent.

Study Design/Methods

A. Animals

Domestic Sus Scrofa male, castrated adolescent pigs weighing between 25 to 30 kg were used in these studies. Pigs were acquired from V. B. Zucht and Mast GmbH, Dorfstraβe 12, 39307 Klein Demsin, Germany. During a ten day (minimum) quarantine period and for four additional days, pigs selected from the animal population were given a corn-based high-fiber feed and unfiltered tap water was provided ad libitum. Samples of the water were analyzed for total dissolved solids, harness, specified microbiological content and selected environmental contaminants. No known contaminants were identified which would be expected to interfere with the study. The animals were held in quarantine for a minimum of ten days to ensure the health of each animal before the initiation of the study.

B. Interventional Procedure and Surgical Preparation

The pigs were pre-sedated by intramuscular injection of ketamine and xylazine. A venous access was provided. After sedation, the animals were intubated and maintained in anesthesia with intravenous 3 to 10 ml Propofol (Recofol® 1% (Curamed Pharma GmbH, Germany)). The pigs were intubated (Endonorm 6.5 F, Rusch GmbH, Germany) and ventilation was started using a mixture of 30 vol. % of pure oxygen, 70 vol % $N_2O$ and 1-2 vol % of Isofluran (Isofluran Curamed®, Curamed Pharma GmbH, Germany). After induction of anesthesia, an incision was made in the neck to expose the carotid artery. An arterial sheath was introduced and advanced into the artery. For the interventional procedure, the animals received 5,000 IU of heparin, 250 mg aspirin intravenously (Aspisol®, Bayer AG, Germany), and intracoronary nitroglycerin.

In each of forty-two pigs, one TriMaxx® stent (P) mounted on a bare angioplasty balloon was implanted in a randomly selected artery, i.e., left anterior descending coronary artery (LAD) or left circumflex coronary artery (CX). The remaining coronary vessel was randomly assigned to receive either: (a) a second TriMaxx® stent on a bare balloon (P), (b) a TriMaxx® stent on a drug-eluting balloon (DEB), or (c) a ZoMaxx® drug eluting stent on a bare balloon (DES). Thus, one set of fourteen pigs received two TriMaxx® stents mounted on bare angioplasty balloons in LAD and CX (P-P), a second set of fourteen pigs received one TriMaxx® stent mounted on a bare angioplasty balloon in one coronary artery and a TriMaxx® stent on a drug eluting balloon in the other artery (P-DEB), and a third set of fourteen pigs received a TriMaxx® stent mounted on a bare angioplasty balloon in one artery and a ZoMaxx® drug eluting stent on a bare angioplasty balloon in the other coronary arty (P-DES).

The placebo control was a TriMaxx® Coronary Stent coated with phosphorylcholine (PC) mounted on a PTCA catheter. The drug eluting stent was a ZoMaxx® Coronary Stent coated with PC and Zotarolimus premounted on a PTCA catheter and the drug eluting balloon was an angioplasty balloon coated with Zotarolimus premounted with a TriMaxx® Coronary Stent.

The coating solution was 0.7 ml ethanol+150 ul Ultravist 370+4.15 ml acetone; thereof 3 ml+135 mg Zotarolimus=45 mg Zotarolimus/ml Zotarolimus. Ethanol content of the solution: 14%. The balloons were coated two times to achieve 13 µl (3.0-17 mm) or 15 µl (3.5-17 mm) by either an automatically adjustable 50 µl or a conventional 25 µl Hamilton syringe. Total consumption/coating step=47×13 µl+59×15 µl+losses=1.5 ml+losses. The drying time between coatings was ≧3 hrs.

TABLE I

Summary of Coating

| Samples | n | µg Zotarolimus | µg/mm² balloon surface | µg/mm balloon length | % of dose |
|---|---|---|---|---|---|
| Unused coated balloons with stents 3.5-17 mm | 5 | 1 200 ± 46 | 6.4 ± 0.2 | 71 ± 3 | 100 |
| Unused coated balloons with stents 3.0-17 mm | 4 | 1072 ± 56 | 6.7 ± 0.3 | 63 ± 3 | 100 |
| Coated balloons after use | 15 | 131 ± 60 | | 7.7 ± 3.5 | 14.1 ± 11.5 |
| Bare balloons with premounted ZoMaxx stents after use | 4 | not detectable | | | |
| Bare balloons with bare stents after use | 3 | not detectable | | | |

The Zotarolimus content of balloons with stents and balloon after stent implantation was calculated and summarized at Table II.

TABLE II

Zotarolimus Content of Balloons With Stents And Balloons After Implantation

| Sample/ Animal no*** | Peak area ABT | Peak area Oxepane | Total area | Conc. ABT µg/ml | ABT-578 µg | % of dose |
|---|---|---|---|---|---|---|
| 25 µg/ml | 722,842 | 43,851 | 766,693 | 25.00 | | |
| 18/3.5-17 | 21 439 952 | 1 620 115 | 23 060 067 | 752 | 1 128 | |
| 31/3.5-17 | 22 734 940 | 1 731 578 | 24 466 518 | 798 | 1 197 | |
| 38/3.5-17 | 23 266 330 | 1 718 515 | 24 984 845 | 815 | 1 222 | |
| 44/3.5-17 | 22 843 718 | 1 669 004 | 24 512 722 | 799 | 1 199 | |
| 54/3.5-17 | 23 859 656 | 1 772 667 | 25 632 323 | 836 | 1 254 | |
| Mean ± SD | | | | | 1 200 ± 46 | |
| 71/3.0-17 | 20 545 884 | 1 629 657 | 22 175 541 | 723 | 1.085 | |
| 72/3.0-17 | 10 559 856 | 1 576 729 | 12 13 585 | 396 | 594 | |
| 88/3.0-17 | 20 479 530 | 1 601 586 | 22 081 116 | 720 | 1.080 | |
| 90/3.0-17 | 18 874 040 | 1 491 887 | 20 365 927 | 664 | 996 | |
| 98/3.0-17 | 21 480 138 | 1 648 244 | 23 128 382 | 754 | 1.131 | |
| Mean ± SD | | | | | 1073 ± 56* | |
| 16**/14 CX | 1 206 986 | 93 207 | 1 300 193 | 42.5 | 63.8 | 5.3 |
| 19/5 CX | 1 186 017 | 101 098 | 1 287 115 | 42.0 | 63.0 | 5.2 |
| 22/43 CX | 2 474 350 | 175 955 | 2 650 305 | 86.7 | 130 | 10.8 |
| 25/20 LAD | 2 266 034 | 159 360 | 2 425 394 | 79.3 | 119 | 9.9 |
| 26/7 CX | 1 129 959 | 71 187 | 1 201 146 | 39.2 | 58.8 | 4.9 |
| 28/2 LAD | 1 817 150 | 143 416 | 1 960 566 | 63.9 | 95.9 | 8.0 |
| 36/32 LAD | 4 119 968 | 300 699 | 4 420.667 | 145 | 217 | 18.1 |
| 37/34-36 LAD | 2 600 973 | 186 731 | 2 787 704 | 91.2 | 137 | 11.4 |
| 43/3 CX | 5 247 028 | 394 311 | 5 641 339 | 184 | 276 | 23.0 |
| 48**/21 CX | 2 621 613 | 195 138 | 2 816 751 | 92.1 | 138 | 11.5 |
| 49/17 LAD | 3 526 794 | 261 929 | 3 788 723 | 124 | 186 | 15.5 |
| 51/19 LAD | 2 996 942 | 221 358 | 3 218 300 | 105 | 158 | 13.2 |
| 53/10 LAD | 2 112 427 | 145 245 | 2 257 672 | 73.8 | 111 | 9.2 |

TABLE II-continued

Zotarolimus Content of Balloons With Stents And Balloons After Implantation

| Sample/Animal no[***] | Peak area ABT | Peak area Oxepane | Total area | Conc. ABT µg/ml | ABT-578 µg | % of dose |
|---|---|---|---|---|---|---|
| 56/24 CX | 2 232 040 | 161 731 | 2 393 771 | 78.3 | 117 | 9.8 |
| 92[**]/13 CX | 1 828 869 | 135 997 | 1 964 866 | 64.3 | 96.4 | 9.0 |
| [**]more blood than on other balloons | | | | | 131 ± 60 | 14.1 ± 11.5 |
| DES/17 | no peak | | | | | |
| DES/23 | no peak | | | | | |
| DES/27 | no peak | | | | | |
| DES/28 | no peak | | | | | |
| No drug/3LAD | no peak | | | | | |
| No drug/19 CX | no peak | | | | | |
| No drug/2CX | no peak | | | | | |

The Zotarolimus measurements were made according to the following method, the gradient clean up was not performed. Zorbax Eclipse XDB-C8 columns sized 4.6×75 mm by 3.5 micrometers, the column temperature of 45 degrees centigrade at a flow rate of 1 ml/min, the flow media 51% ammonia acetate buffer ph 4.9; 49% acetone nitrile, injection volume 20 micro liters, UV detection 278 nm.

Each stent delivery system was prepared by flushing the guidewire lumen with heparinized saline solution. Air was aspirated from the balloon lumen using negative pressure, filling lumen with a 50/50 mixture of 0.9% normal saline and contrast solution. Stents were then introduced into the coronary arteries by advancing the stented balloon catheter through the guide catheter and over the guidewire to the deployment site within the LAD or CX. The balloon was then inflated at a steady rate to a pressure sufficient to target a stent: artery ratio of 1.2. Confirmation of this stent-artery ratio was made when the angiographic images were quantitatively assessed. After the target balloon to artery ratio was achieved for 60 seconds, vacuum was applied to the inflation device in order to deflate the balloon. The delivery system was removed.

Contrast injections were used to determine device patency and additional acute system was noted. This process was repeated until all devices were deployed. All catheters were then removed from the animal and the carotid artery was ligated. At this time, blood pressure monitoring was terminated. The incision was closed in layers with suture materials. The skin was closed with closure materials. The pigs were returned to their cages and allowed to recover from anesthesia. To prevent infection, pigs were given Urocyclin 10% at appropriate dosage levels at least 1 day prior to implantation and on the day of implantation. Additional doses were administered as necessary.

After 28 days, the pigs were sacrificed using pentobarbital in deep anesthesia. Hearts were rapidly excised, the coronary system flushed with 0.9% saline and the arteries fixed by perfusion with 4% buffered formalin under physiological pressure and overnight immersion. The target segments were then dissected and samples for histology obtained.

C. Data Collection

1. Semi-Quantitative and Quantitative Coronary Analysis (QCA)

Coronary imaging was done using a Philips PolyArc fluoroscope connected to a digitizer using an Apple Macintosch Power PC. A semi-quantitative evaluation of coronary angiography was performed with the following grading: 0=no signs of neointimal hyperplasia (identical with result immediately after stent implantation); 1=slight signs of neointimal hyperplasia; 2=moderate signs of neointimal hyperplasia (minimal lumen diameter in-stent identical with vessel reference diameter); 3=clear signs of neointimal hyperplasia (minimal lumen diameter in-stent identical with vessel reference diameter); 4=strong signs of neointimal hyperplasia, about 50% of reference diameter; and 5=distinct signs of neointimal hyperplasia (vessel nearly or totally occluded). The CAAS II for Research System (Pie Medical, the Netherlands) was used for quantitative coronary analysis.

2. Histology

Hearts were rapidly excised, the coronary system flushed with 0.9% saline and the arteries fixed by perfusion with 4% buffered formalin under physiological pressure and overnight immersion. Stented coronary arteries were dissected from the formalin-fixed hearts and immersed in methyl-methacrylate (Merck, Darmstadt, Germany). Three representative cross sectiosn per stent were separated from the blocks with a rotation microtome (Leica RM 2255), polished, and glued on acrylic plastic slides. Final specimens were stained by HE and Masson-Goldner technique. After digitalizing, histomorphometric measurements were taken with the NIH image program (PC version 'Scion Image,' Scion Corporation, Maryland, USA). The evaluated parameters were: luminal area, external elastic lamina (EEL) diameter, maximal neointimal thickness, EEL area, luminal area, and neointimal area.

Histomorphometric variables of the three cross-sectional planes were averaged to obtain a mean value per stent. Continuous variables were compared by ANOVA analysis using the software package SPSS 13.0 for Windows (SPSS Inc. Chicago, Ill.). Data are presented as the mean value±SD.

D. Results

1. Semi-quantitative angiographic coronary analysis

Figure 7:
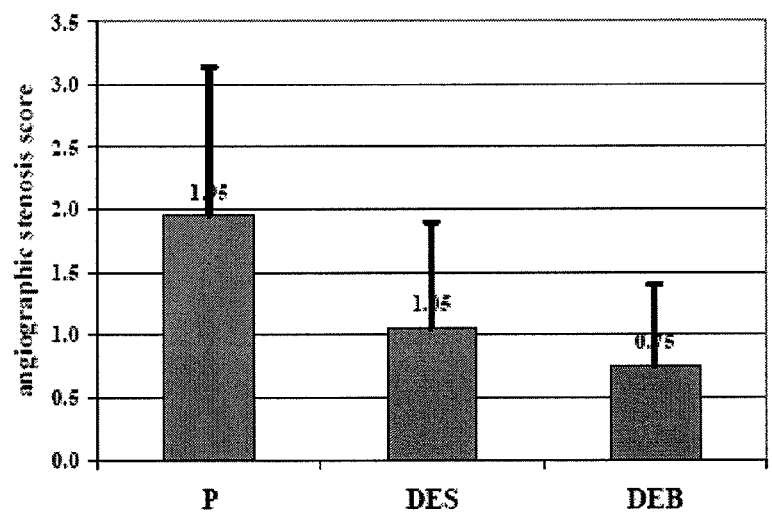
FIG. 7 depicts a graph illustrating the comparative results of semi-quantitative angiographic scoring (narrowed compared to reference diameter score >1) of P (TriMaxx Stent on uncoated balloon), DEB (TriMaxx Stent on Zotarolimus coated balloon), and DES (ZoMaxx stent on uncoated balloon), as described in the Comparative Studies. An arbitrary scoring system was used in which 0=still oversized, 1=about reference diameter, 2=slightly less than reference diameter, 3=significantly less than reference diameter, 4=very narrow but not included, 5=occluded.

FIG. 7 illustrates the comparative results of semi-quantitative angiographic scoring (narrowed compared to reference diameter score >1) of P (TriMaxx Stent on uncoated balloon), DEB (TriMaxx Stent on Zotarolimus coated balloon), and DES (ZoMaxx stent on uncoated balloon). An arbitrary scoring system was used in which 0=still oversized, 1=about reference diameter, 2=slightly less than reference diameter, 3=significantly less than reference diameter, 4=very narrow but not included, 5=occluded. As illustrated in FIG. 7, the angiographic stenosis score reveals a reduction of stenosis by the drug eluting stent (DES) and a further improved reduction of stenosis of the Zotarolimus coated balloon (DEB) after one month.

Table III below summarizes the individual results of the semiquantitative angiographic scoring.

TABLE III

Individual Results of Semi-Quantitative Angiographic Scoring

| Animal number | Vessel | | Vessel | |
|---|---|---|---|---|
| # 7 | LAD | 3-4 | CX | 0 |
| # 8 | LAD | 2 | CX | 2 |
| # 9 | LAD | 3-4 | CX | 0-1 |
| # 10 died shortly after the intervention | | | | |
| # 11 | LAD | 3 | CX | 1 |
| # 12 | LAD | 3 | CX | 1 |
| # 13 | LAD | 2 | CX | 0 |
| # 14 | LAD | 4 | CX | occlusion several cm to stent, infarction |
| # 15 | LAD | 4 | CX | 1 |
| # 16 | LAD | 0-1 | CX | 1 |
| # 17 | LAD | 3 | CX | 2 |
| # 18 | LAD | 2-3 | CX | 1 |
| # 19 | LAD | 1 | CX | 1 |
| # 20 | LAD | 3-4 | CX | 0 |
| # 21 | LAD | 4 | CX | 1-2 |
| # 22 | LAD | 1 | CX | 3 |
| # 23 | LAD | (0)-1 | CX | 1 |
| # 24 | LAD | 1 | CX | 1 |
| # 25 | LAD | (0)-1 | CX | 2 |
| # 26 | LAD | 1 | CX | 1 |
| # 27 | LAD | 1(–2) | CX | 0 |
| # 28 | LAD | 1 | CX | 1 |
| # 29 | LAD | 3 | CX | 0 |
| # 30 | LAD | 4 | CX | 0 |
| # 31 | LAD | 4 | CX | (0)-1 |
| # 32 | LAD | 1 | CX | 2 |
| # 33 | LAD | 3(–4) | CX | 3 |
| # 34 | LAD | 1-2 | CX | 1 |
| # 35 | LAD | 2 | CX | (0)-1 |
| # 36 | LAD | 1 (–2) | CX | 1 |
| # 37 | LAD | 1 (–2) | CX | (0)-1 |
| # 38 died shortly after the intervention | | | | |
| # 39 | LAD | 1-(2) | CX | 1 |
| # 40 | LAD | (0)-1 | CX | 0 |
| # 41 | LAD | 3-4 | CX | 0-1 |
| # 42 | LAD | 1-2 | CX | 0 |
| # 43 | LAD | 2-3 | CX | 0-1 |
| # 44 | LAD | 1-2 | CX | 3 |
| # 45 | LAD | 1-2 | CX | 0 |
| # 46 | LAD | 3 | CX | 1 |
| # 47 | LAD | 3 | CX | 1 |
| # 48 | LAD | 1 | CX | 0-1 |
| # 49 | LAD | 1-2 | CX | 1-2 |
| # 50 | LAD | 3-4 | CX | 1 |

Individual results of semi quantitative angiographic scoring, 0 = still oversized, 1 = about reference diameter, 2 = slightly less than reference diameter, 3 significantly less than reference diameter, 4 = very narrow but not occluded, 5 = occluded. Treatment: Placebo (no drug), DES, DEB.

2. Quantitative Coronary Angiography (QCA)

Figure 8:
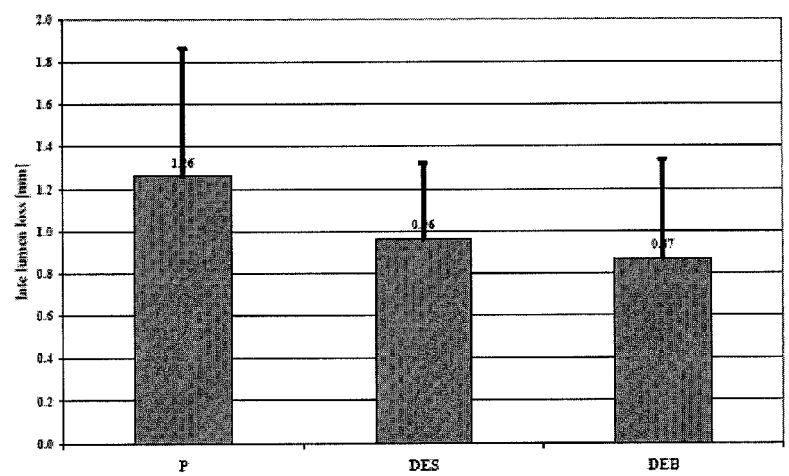
FIG. 8 depicts a graph showing a summary of the results of late lumen loss [mm] assessed by QCA of P (TriMaxx Stent on uncoated balloon), DEB (TriMaxx Stent on Zotarolimus coated balloon), and DES (ZoMaxx stent on uncoated balloon), as described in the Comparative Studies.

As illustrated in Tables IV, V, and VI below, QCA reveals a reduction of late lumen loss by the Zotarolimus coated stent and the Zotarolimus coated balloon. A summary of the late lumen loss as assessed by QCA for the P, DES and DEB treatments is also shown in FIG. 8.

TABLE IV

Results of QCA

| | P | DES | DEB | p |
|---|---|---|---|---|
| | stent implantation | | | |
| RFD [mm] | 2.30 ± 0.37 | 2.22 ± 0.39 | 2.33 ± 0.33 | 0.688 |
| stent diameter [mm] | 2.69 ± 0.31 | 2.66 ± 0.28 | 2.64 ± 0.26 | 0.826 |
| overstretch [—] | 1.18 ± 0.15 | 1.22 ± 0.17 | 1.14 ± 0.11 | 0.380 |
| | control angiography | | | |
| RFD control [mm] | 2.38 ± 0.27 | 2.31 ± 0.23 | 2.31 ± 0.30 | 0.463 |
| MLD control [mm] | 1.44 ± 0.58 | 1.69 ± 0.45 | 1.77 ± 0.49 | 0.126 |
| late lumen loss [mm] | 1.26 ± 0.61 | 0.96 ± 0.36 | 0.87 ± 0.47 | 0.028 |

RFD = reference diameter at baseline [mm], stent diameter [mm], overstretch ratio [—], RFD at control [mm], MLD minimal lumen diameter at control [mm], and late lumen loss [mm]. ANOVA analysis.

TABLE V p-Values of QCA

| | p P vs DES | p P vs DEB | p DES vs DEB |
|---|---|---|---|
| RFD [mm] | 0.460 | 0.790 | 0.421 |
| stent diameter [mm] | 0.732 | 0.575 | 0.853 |
| overstretch [—] | 0.432 | 0.329 | 0.167 |
| RFD control [mm] | 0.323 | 0.351 | 0.994 |
| MLD control [mm] | 0.125 | 0.122 | 0.978 |
| late lumen loss [mm] | 0.084 | 0.027 | 0.550 |

TABLE VI

Results of QCA for LAD only

| only LAD | P | DES | DEB | p |
|---|---|---|---|---|
| | stent implantation | | | |
| RFD [mm] | 2.17 ± 0.28 | 2.01 ± 0.33 | 2.13 ± 0.19 | 0.409 |
| stent diameter [mm] | 2.59 ± 0.22 | 2.58 ± 0.24 | 2.55 ± 0.24 | 0.898 |
| overstretch [—] | 1.21 ± 0.18 | 1.31 ± 0.21 | 1.20 ± 0.10 | 0.395 |
| | control angiography | | | |
| RFD control [mm] | 2.32 ± 0.24 | 2.15 ± 0.10 | 2.16 ± 0.24 | 0.110 |
| MLD control [mm] | 1.18 ± 0.50 | 1.42 ± 0.38 | 1.42 ± 0.38 | 0.318 |
| late lumen loss [mm] | 1.41 ± 0.61 | 1.15 ± 0.37 | 1.13 ± 0.37 | 0.328 |

TABLE VII

Results of QCA for CX only

| only CX | P | DES | DEB | p |
|---|---|---|---|---|
| | stent implantation | | | |
| RFD [mm] | 2.44 ± 0.40 | 2.43 ± 0.35 | 2.53 ± 0.31 | 0.829 |
| stent diameter [mm] | 2.78 ± 0.36 | 2.73 ± 0.33 | 2.73 ± 0.26 | 0.886 |
| overstretch [—] | 1.15 ± 0.11 | 1.13 ± 0.05 | 1.08 ± 0.09 | 0.242 |
| | control angiography | | | |
| RFD control [mm] | 2.45 ± 0.28 | 2.46 ± 0.23 | 2.46 ± 0.29 | 0.997 |
| MLD control [mm] | 1.69 ± 0.54 | 1.96 ± 0.35 | 2.12 ± 0.29 | 0.235 |
| late lumen loss [mm] | 1.11 ± 0.57 | 0.77 ± 0.22 | 0.60 ± 0.43 | 0.153 |

Tables VIII and IX summarize the individual results of QCA for the animals in the study.

TABLE VIII

Individual QCA Results for animals G59/007-G59/028

| ID | group | RFD | Stent | RFD control | MLD control | over-stretch | late loss |
|---|---|---|---|---|---|---|---|
| G59007cx | P | 2.42 | 2.71 | 2.41 | 1.68 | 1.12 | 1.03 |
| G59007lad | P | 2.31 | 2.58 | 2.20 | 0.82 | 1.12 | 1.76 |

TABLE VIII-continued

Individual QCA Results for animals G59/007-G59/028

| ID | group | RFD Stent | RFD control | MLD control | over-stretch | late loss |
|---|---|---|---|---|---|---|
| G59008cx | P | 2.14 2.62 | 2.28 | 1.50 | 1.22 | 1.12 |
| G59008lad | DEB | 2.13 2.54 | 1.99 | 1.26 | 1.19 | 1.28 |
| G59009cx | DEB | 2.30 2.78 | 2.21 | 2.35 | 1.21 | 0.43 |
| G59009lad | P | 1.94 2.42 | 2.16 | 0.98 | 1.25 | 1.44 |
| G59010cx | P | | | | | |
| G59010lad | P | | | | | |
| G59011cx | DEB | 2.63 2.89 | 2.22 | 2.25 | 1.10 | 0.64 |
| G59011lad | P | 2.19 2.61 | 1.78 | 0.85 | 1.19 | 1.76 |
| G59012cx | P | 2.80 3.22 | 2.63 | 1.88 | 1.15 | 1.34 |
| G59012lad | P | 2.52 2.78 | 2.67 | 0.86 | 1.10 | 1.92 |
| G59013cx | DEB | 2.59 2.76 | 2.59 | 1.57 | 1.07 | 1.19 |
| G59013lad | P | 2.24 2.66 | 2.39 | 1.42 | 1.19 | 1.24 |
| G59014cx | P | 2.53 2.93 | 2.53 | 0.01 | 1.16 | 2.92 |
| G59014lad | P | 1.91 2.58 | 2.54 | 0.84 | 1.35 | 1.74 |
| G59015cx | P | 2.40 2.91 | 2.31 | 1.84 | 1.21 | 1.07 |
| G59015lad | P | 1.84 2.91 | 1.73 | 0.20 | 1.58 | 2.71 |
| G59016cx | P | 3.07 3.18 | 3.11 | 2.20 | 1.04 | 0.98 |
| G59016lad | DEB | 2.42 2.73 | 2.29 | 1.71 | 1.13 | 1.02 |
| G59017cx | P | 1.92 2.72 | 1.99 | 1.09 | 1.42 | 1.63 |
| G59017lad | P | 2.57 2.69 | 2.45 | 1.59 | 1.05 | 1.10 |
| G59018cx | P | 2.39 2.52 | 2.60 | 1.95 | 1.05 | 0.57 |
| G59018lad | P | 2.23 2.53 | 2.46 | 1.27 | 1.13 | 1.26 |
| G59019cx | DEB | 2.51 2.89 | 2.65 | 2.31 | 1.15 | 0.58 |
| G59019lad | P | 2.39 2.68 | 2.21 | 1.22 | 1.12 | 1.46 |
| G59020cx | DEB | 2.47 2.70 | 2.35 | 1.99 | 1.09 | 0.71 |
| G59020lad | P | 2.12 2.51 | 2.16 | 1.08 | 1.18 | 1.43 |
| G59021cx | P | 2.48 2.48 | 2.74 | 1.56 | 1.00 | 0.92 |
| G59021lad | P | 2.25 2.41 | 2.51 | 1.15 | 1.07 | 1.26 |
| G59022cx | P | 2.00 2.38 | 2.04 | 1.08 | 1.19 | 1.30 |
| G59022lad | P | 2.30 2.56 | 2.48 | 1.99 | 1.11 | 0.57 |
| G59023cx | P | 2.59 2.87 | 2.42 | 1.62 | 1.11 | 1.25 |
| G59023lad | DEB | 1.79 2.23 | 2.13 | 1.08 | 1.25 | 1.15 |
| G59024cx | P | 2.76 2.92 | 2.64 | 2.68 | 1.06 | 0.24 |
| G59024lad | P | 2.47 2.62 | 2.45 | 2.28 | 1.06 | 0.34 |
| G59025cx | P | 1.85 2.18 | 2.13 | 1.38 | 1.18 | 0.80 |
| G59025lad | DEB | 2.11 2.35 | 2.50 | 1.89 | 1.11 | 0.46 |
| G59026cx | P | 2.72 2.93 | 2.76 | 2.18 | 1.08 | 0.75 |
| G59026lad | DEB | 2.05 2.82 | 2.24 | 1.83 | 1.38 | 0.99 |
| G59027cx | DEB | 2.11 2.16 | 2.97 | 2.36 | 1.02 | −0.20 |
| G59027lad | P | 2.26 2.48 | 2.30 | 1.90 | 1.10 | 0.58 |
| G59028cx | P | 2.22 2.54 | 2.35 | 1.18 | 1.14 | 1.36 |
| G59028lad | DES | 2.09 2.32 | 2.24 | 1.33 | 1.11 | 0.99 |

TABLE IX

Individual QCA Results for animals G59/029-G59/050

| ID | group | RFD | Stent | RFD control | MLD control | overstretch |
|---|---|---|---|---|---|---|
| G59029cx | DES | 2.16 | 2.53 | 2.34 | 1.71 | 1.17 |
| G59029lad | P | 1.50 | 2.55 | 2.33 | 1.18 | 1.70 |
| G59030cx | DEB | 3.12 | 2.90 | 2.21 | 2.02 | 0.93 |
| G59030lad | P | 2.57 | 2.40 | 2.56 | 0.69 | 0.93 |
| G59031cx | DES | 2.72 | 2.82 | 2.94 | 2.35 | 1.04 |
| G59031lad | P | 2.10 | 2.73 | 2.39 | 0.89 | 1.30 |
| G59032cx | P | 2.53 | 2.61 | 2.69 | 0.83 | 1.03 |
| G59032lad | P | 1.97 | 2.36 | 2.65 | 2.05 | 1.20 |
| G59033cx | P | 1.85 | 2.15 | 2.05 | 1.38 | 1.16 |
| G59033lad | DES | 1.76 | 2.40 | 2.01 | 0.67 | 1.36 |
| G59034cx | P | 2.12 | 2.29 | 2.18 | 1.74 | 1.08 |
| G59034lad | DES | 2.15 | 2.45 | 2.22 | 1.87 | 1.14 |
| G59035cx | P | 2.63 | 2.84 | 2.72 | 2.36 | 1.08 |
| G59035lad | DES | 2.43 | 2.71 | 2.30 | 1.35 | 1.12 |
| G59036cx | P | 1.97 | 2.44 | 2.24 | 2.24 | 1.24 |
| G59036lad | P | 2.03 | 2.23 | 2.57 | 1.70 | 1.10 |
| G59037cx | P | 2.57 | 3.33 | 2.84 | 2.26 | 1.30 |
| G59037lad | P | 2.36 | 2.66 | 2.36 | 1.77 | 1.13 |
| G59038cx | P | | | | | |
| G59038lad | DEB | | | | | |
| G59039cx | DES | 2.00 | 2.32 | 2.38 | 1.45 | 1.16 |
| G59039lad | P | 2.18 | 2.60 | 2.08 | 1.12 | 1.19 |

TABLE IX-continued

Individual QCA Results for animals G59/029-G59/050

| ID | group | RFD | Stent | RFD control | MLD control | overstretch |
|---|---|---|---|---|---|---|
| G59040cx | P | 3.06 | 3.16 | 2.59 | 2.09 | 1.03 |
| G59040lad | DES | 1.95 | 2.77 | 2.09 | 1.64 | 1.42 |
| G59041cx | DES | 3.03 | 3.33 | 2.32 | 2.21 | 1.10 |
| G59041lad | P | 2.71 | 3.20 | 2.34 | 1.16 | 1.18 |
| G59042cx | P | 2.42 | 2.64 | 2.55 | 1.98 | 1.09 |
| G59042lad | DEB | 2.24 | 2.80 | 2.22 | 1.16 | 1.25 |
| G59043cx | DES | 2.25 | 2.53 | 2.54 | 1.63 | 1.12 |
| G59043lad | P | 2.51 | 2.74 | 2.45 | 0.36 | 1.09 |
| G59044cx | P | 3.59 | 3.65 | 2.72 | 1.57 | 1.02 |
| G59044lad | DES | 2.27 | 2.96 | 2.15 | 1.58 | 1.30 |
| G59045cx | DES | 2.52 | 2.87 | 2.37 | 2.21 | 1.14 |
| G59045lad | P | 1.97 | 2.39 | 2.16 | 1.23 | 1.21 |
| G59046cx | DES | 2.33 | 2.72 | 2.32 | 2.17 | 1.17 |
| G59046lad | P | 1.99 | 2.38 | 2.42 | 0.89 | 1.20 |
| G59047cx | P | 2.67 | 3.03 | 2.37 | 1.67 | 1.13 |
| G59047lad | P | 1.91 | 2.38 | 2.24 | 1.04 | 1.25 |
| G59048cx | P | 2.22 | 2.76 | 2.40 | 1.97 | 1.24 |
| G59048lad | DES | 1.45 | 2.44 | 2.07 | 1.53 | 1.68 |
| G59049cx | P | 2.01 | 2.80 | 2.23 | 1.61 | 1.39 |
| G59049lad | DEB | 2.20 | 2.35 | 1.73 | 0.99 | 1.07 |
| G59050cx | P | 2.60 | 3.39 | 2.12 | 1.72 | 1.30 |
| G59050lad | P | 1.82 | 3.08 | 1.83 | 0.64 | 1.69 |

3. Histomorphometry

Figure 9:
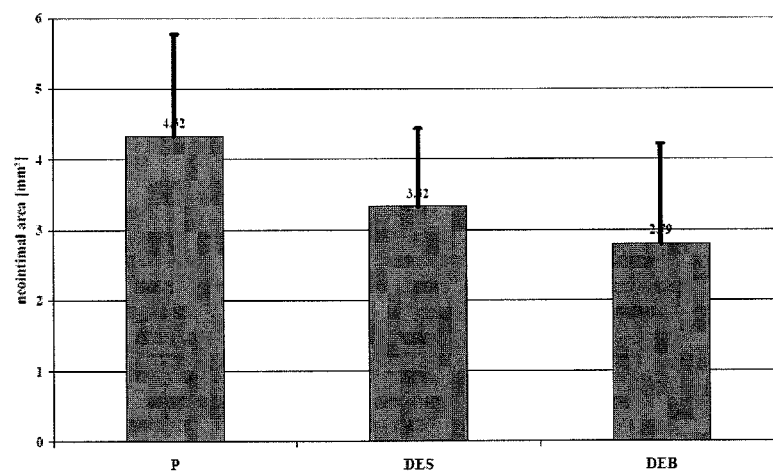
FIG. 9 depicts a graph showing a summary of the results of neointimal area [mm] assessed by histomorphometry of P (TriMaxx Stent on uncoated balloon), DEB (TriMaxx Stent on Zotarolimus coated balloon), and DES (ZoMaxx stent on uncoated balloon), as described in the Comparative Studies.

As represented in Tables X, XI, XII, and XIII, histomorphometry revealed a significant reduction of neointimal formation by the Zotarolimus coated balloon and Zotarolimus coated stent. A summary of the neointimal area for the P, DES and DEB treatments is also shown in FIG. 9.

TABLE X

Results of Histomorphmetry

| | P | DES | DEB | p |
|---|---|---|---|---|
| n | 56 | 14 | 14 | all |
| vessel diameter [mm] | 3.07 ± 0.16 | 2.94 ± 0.17 | 3.07 ± 0.16 | 0.041 |
| lumen diameter [mm] | 1.93 ± 0.48 | 2.15 ± 0.35 | 2.20 ± 0.37 | 0.059 |
| max. neoint. thickn. [mm] | 0.63 ± 0.37 | 0.38 ± 0.21 | 0.49 ± 0.46 | 0.055 |
| vessel area [mm$^2$] | 7.44 ± 0.79 | 7.05 ± 0.49 | 7.17 ± 1.08 | 0.196 |
| luminal area [mm$^2$] | 3.12 ± 1.25 | 3.73 ± 0.98 | 4.38 ± 1.37 | 0.003 |
| neointimal area [mm$^2$] | 4.32 ± 1.45 | 3.32 ± 1.11 | 2.79 ± 1.43 | 0.001 |
| area stenosis [%] | 58% ± 17% | 47% ± 13% | 38% ± 19% | 0.001 |
| injury score [—] | 1.20 ± 0.86 | 1.25 ± 0.92 | 1.16 ± 0.43 | 0.961 |
| inflammation score [—] | 1.45 ± 0.94 | 1.65 ± 0.90 | 0.75 ± 0.86 | 0.021 |

Vessel diameter [mm], lumen diameter [mm], maximal neointimal thickness [mm], vessel area [mm$^2$], area stenosis [%], injury score [—], and inflammation score [—]. ANOVA analysis.

TABLE XI

Comparison of p-Values of Histomorphometry

| n | p P vs DES | p P vs DEB | p DES vs DEB |
|---|---|---|---|
| vessel diameter [mm] | 0.015 | 0.943 | 0.054 |
| lumen diameter [mm] | 0.109 | 0.052 | 0.717 |
| max. neoint. thickn. [mm] | 0.018 | 0.213 | 0.453 |
| vessel area [mm$^2$] | 0.083 | 0.286 | 0.715 |
| luminal area [mm$^2$] | 0.096 | 0.002 | 0.161 |
| neointimal area [mm$^2$] | 0.019 | 0.001 | 0.281 |
| area stenosis [%] | 0.028 | 0.001 | 0.186 |
| injury score [—] | 0.844 | 0.885 | 0.752 |
| inflammation score [—] | 0.482 | 0.013 | 0.012 |

TABLE XII

Results of Histomorphometry for CX only

| | only CX | | | |
|---|---|---|---|---|
| | P | DES | DEB | p |
| n | 28 | 7 | 7 | |
| vessel diameter [mm] | 3.01 ± 0.17 | 2.85 ± 0.20 | 3.01 ± 0.17 | 0.109 |
| lumen diameter [mm] | 1.93 ± 0.53 | 2.17 ± 0.17 | 2.23 ± 0.50 | 0.426 |
| max. neoint. thickn. [mm] | 0.53 ± 0.32 | 0.34 ± 0.11 | 0.33 ± 0.29 | 0.254 |
| vessel area [mm$^2$] | 7.16 ± 0.85 | 6.74 ± 0.42 | 6.96 ± 1.14 | 0.489 |
| luminal area [mm$^2$] | 3.33 ± 1.32 | 3.74 ± 0.50 | 4.24 ± 1.71 | 0.246 |
| neointimal area [mm$^2$] | 3.83 ± 1.38 | 3.00 ± 0.55 | 2.72 ± 1.56 | 0.087 |
| area stenosis [%] | 53% ± 17% | 44% ± 7% | 39% ± 22% | 0.106 |
| injury score [—] | 1.23 ± 0.91 | 1.14 ± 0.66 | 1.19 ± 0.23 | 0.963 |
| inflammation score [—] | 1.48 ± 1.06 | 1.57 ± 0.63 | 0.71 ± 0.81 | 0.157 |

TABLE XIII

Results of Histomorphometry for LAD only

| | only LAD | | | |
|---|---|---|---|---|
| | P | DES | DEB | p |
| n | 28 | 7 | 7 | |
| vessel diameter [mm] | 3.12 ± 0.14 | 3.03 ± 0.07 | 3.13 ± 0.14 | 0.258 |
| lumen diameter [mm] | 1.93 ± 0.41 | 2.13 ± 0.48 | 2.17 ± 0.22 | 0.110 |
| max. neoint. thickn. [mm] | 0.73 ± 0.39 | 0.43 ± 0.29 | 0.64 ± 0.57 | 0.221 |
| vessel area [mm$^2$] | 7.73 ± 0.62 | 7.36 ± 0.32 | 7.38 ± 1.06 | 0.285 |
| luminal area [mm$^2$] | 2.91 ± 1.17 | 3.72 ± 1.35 | 4.52 ± 1.06 | 0.007 |
| neointimal area [mm$^2$] | 4.82 ± 1.37 | 3.65 ± 1.46 | 2.86 ± 1.41 | 0.004 |
| area stenosis [%] | 62% ± 15% | 49% ± 18% | 38% ± 18% | 0.002 |
| injury score [—] | 1.16 ± 0.83 | 1.36 ± 1.17 | 1.14 ± 0.59 | 0.856 |
| inflammation score [—] | 1.43 ± 0.81 | 1.73 ± 1.16 | 0.79 ± 0.98 | 0.139 |

Tables XIV and XV summarize the individual results of histomorphometry.

TABLE XIV

Individual Results of Histomorphometry for animals G59/007-G59/028

| ID | group | vesdia | lumdia | max thick | vesaria | lumarea | neoint | area stenosis | injury | inflammation |
|---|---|---|---|---|---|---|---|---|---|---|
| G59007cx | P | 3.10 | 2.33 | 0.40 | 7.70 | 4.29 | 3.41 | 44.3% | 0.50 | 0.44 |
| G59007lad | P | 3.17 | 1.39 | 1.09 | 7.89 | 1.53 | 6.36 | 80.6% | 0.20 | 0.22 |
| G59008cx | P | 3.02 | 1.93 | 0.66 | 7.19 | 2.89 | 4.30 | 59.9% | 0.90 | 0.22 |
| G59008lad | DEB | 3.32 | 1.91 | 0.63 | 8.56 | 4.75 | 3.81 | 44.5% | 0.86 | 1.33 |
| G59009cx | DEB | 3.04 | 2.32 | 0.48 | 7.26 | 3.28 | 3.98 | 54.8% | 0.90 | 0.44 |
| G59009lad | P | 3.32 | 2.40 | 0.38 | 8.59 | 4.55 | 4.04 | 47.1% | 0.20 | 0.44 |
| G59010cx | P | | | | | | | | | |
| G59010lad | P | | | | | | | | | |
| G59011cx | DEB | 2.98 | 1.15 | 0.93 | 6.92 | 1.33 | 5.59 | 80.8% | 1.29 | 1.00 |
| G59011lad | P | 3.09 | 2.14 | 0.38 | 6.99 | 3.34 | 3.65 | 52.3% | 0.10 | 0.56 |
| G59012cx | P | 3.21 | 2.02 | 0.66 | 7.92 | 3.24 | 4.68 | 59.1% | 1.00 | 0.44 |
| G59012lad | P | 3.19 | 1.48 | 0.96 | 7.93 | 1.84 | 6.10 | 76.8% | 2.00 | 2.33 |
| G59013cx | DEB | 3.11 | 2.52 | 0.14 | 7.57 | 5.57 | 2.00 | 26.4% | 1.11 | 0.22 |
| G59013lad | P | 3.14 | 1.94 | 0.68 | 7.59 | 2.97 | 4.63 | 60.9% | 1.30 | 1.56 |
| G59014cx | P | 3.12 | 0.01 | 1.50 | 7.44 | 0.01 | 7.43 | 99.9% | 3.00 | 3.00 |
| G59014lad | P | 3.41 | 1.33 | 1.61 | 9.65 | 1.31 | 8.35 | 86.5% | 3.00 | 3.00 |
| G59015cx | P | 3.07 | 1.89 | 0.73 | 7.59 | 2.84 | 4.74 | 62.5% | 1.30 | 1.00 |
| G59015lad | P | 3.16 | 0.75 | 1.99 | 8.07 | 0.44 | 7.64 | 94.6% | 1.80 | 2.44 |
| G59016cx | P | 3.28 | 2.45 | 0.30 | 8.30 | 4.74 | 3.56 | 42.9% | 0.10 | 0.22 |
| G59016lad | DEB | 3.25 | 2.28 | 0.35 | 8.13 | 4.41 | 3.72 | 45.8% | 0.40 | 0.44 |
| G59017cx | P | 2.78 | 1.16 | 0.88 | 5.96 | 1.04 | 4.92 | 82.6% | 1.90 | 1.56 |
| G59017lad | P | 3.15 | 1.74 | 0.71 | 7.75 | 2.47 | 5.28 | 68.1% | 0.80 | 0.78 |
| G59018cx | P | 2.86 | 2.12 | 0.31 | 6.10 | 3.37 | 2.73 | 44.8% | 0.40 | 0.44 |
| G59018lad | P | 2.78 | 1.84 | 0.71 | 7.45 | 2.71 | 4.74 | 63.6% | 1.20 | 1.11 |
| G59019cx | DEB | 2.66 | 2.21 | 0.17 | 4.51 | 3.46 | 1.06 | 23.4% | 1.00 | 0.22 |
| G59019lad | P | 3.22 | 1.94 | 0.77 | 8.01 | 2.94 | 5.07 | 63.3% | 0.70 | 0.89 |
| G59020cx | DEB | 3.01 | 2.28 | 0.27 | 6.87 | 4.15 | 2.72 | 39.5% | 1.11 | 0.22 |
| G59020lad | P | 3.19 | 2.03 | 0.65 | 8.27 | 3.36 | 4.91 | 59.4% | 0.60 | 0.78 |
| G59021cx | P | 2.85 | 1.96 | 0.47 | 6.33 | 3.10 | 3.23 | 51.1% | 0.80 | 0.44 |
| G59021lad | P | 3.01 | 1.79 | 0.61 | 7.19 | 2.72 | 4.47 | 62.2% | 0.60 | 0.67 |
| G59022cx | P | 2.61 | 1.64 | 0.48 | 5.30 | 2.29 | 3.01 | 56.9% | 1.10 | 0.78 |
| G59022lad | P | 3.01 | 2.13 | 0.46 | 7.02 | 3.43 | 3.59 | 51.2% | 0.50 | 0.78 |
| G59023cx | P | 3.11 | 1.78 | 0.67 | 7.48 | 2.54 | 4.95 | 66.1% | 1.00 | 1.00 |
| G59023lad | DEB | 3.09 | 2.07 | 0.49 | 7.65 | 3.43 | 4.22 | 55.2% | 1.10 | 0.44 |
| G59024cx | P | 2.97 | 2.43 | 0.15 | 6.45 | 4.35 | 2.10 | 32.6% | 0.10 | 0.11 |
| G59024lad | P | 3.22 | 2.67 | 0.13 | 8.05 | 5.71 | 2.34 | 29.0% | 0.40 | 0.00 |
| G59025cx | P | 3.14 | 1.65 | 1.12 | 7.97 | 2.21 | 5.76 | 72.3% | 1.50 | 1.22 |
| G59025lad | DEB | 3.15 | 2.20 | 0.53 | 7.77 | 5.39 | 2.38 | 30.6% | 0.50 | 0.22 |
| G59026cx | P | 3.12 | 2.41 | 0.24 | 7.63 | 4.79 | 2.84 | 37.2% | 0.00 | 0.00 |
| G59026lad | DEB | 3.07 | 2.52 | 0.16 | 7.62 | 5.68 | 1.93 | 25.4% | 1.00 | 0.00 |
| G59027cx | DEB | 3.14 | 2.60 | 0.13 | 7.71 | 5.92 | 1.79 | 23.2% | 0.75 | 0.33 |
| G59027lad | P | 3.27 | 2.10 | 0.55 | 8.28 | 3.65 | 4.62 | 55.9% | 0.80 | 0.89 |
| G59028cx | P | 2.75 | 1.84 | 0.36 | 5.79 | 2.77 | 3.01 | 52.1% | 1.60 | 1.44 |
| G59028lad | DES | 2.98 | 2.40 | 0.24 | 7.10 | 4.48 | 2.63 | 37.0% | 0.20 | 0.22 |

TABLE XV

Individual Results of Histomorphometry for animals G59/029-G59/050

| ID | group | vesdia | lumdia | max thick | vesaria | lumarea | neoint | area stenosis | injury | inflammation |
|---|---|---|---|---|---|---|---|---|---|---|
| G59029cx | DES | 2.93 | 2.01 | 0.41 | 6.78 | 3.29 | 3.49 | 51.4% | 0.70 | 0.89 |
| G59029lad | P | 2.93 | 1.71 | 0.71 | 6.67 | 2.27 | 4.40 | 66.0% | 1.70 | 1.11 |
| G59030cx | DEB | 3.19 | 2.51 | 0.22 | 7.87 | 5.95 | 1.92 | 24.4% | 0.80 | 2.44 |
| G59030lad | P | 3.12 | 1.60 | 0.90 | 7.68 | 2.17 | 5.51 | 71.8% | 0.90 | 1.00 |
| G59031cx | DES | 3.03 | 2.46 | 0.19 | 7.28 | 4.66 | 2.62 | 36.0% | 0.60 | 2.22 |
| G59031lad | P | 3.14 | 1.52 | 0.98 | 7.46 | 2.00 | 5.46 | 73.2% | 2.70 | 2.78 |
| G59032cx | P | 2.69 | 1.72 | 0.58 | 5.99 | 2.34 | 3.65 | 60.9% | 2.80 | 2.56 |
| G59032lad | P | 3.10 | 2.40 | 0.44 | 7.73 | 4.52 | 3.22 | 41.6% | 0.20 | 2.67 |
| G59033cx | P | 3.19 | 1.79 | 0.92 | 8.41 | 2.65 | 5.76 | 68.5% | 3.00 | 3.00 |
| G59033lad | DES | 3.10 | 1.16 | 1.02 | 7.84 | 1.11 | 6.73 | 85.9% | 3.00 | 3.00 |
| G59034cx | P | 2.83 | 2.19 | 0.25 | 6.19 | 3.67 | 2.53 | 40.8% | 0.40 | 2.78 |
| G59034lad | DES | 3.04 | 2.37 | 0.24 | 7.30 | 4.36 | 2.95 | 40.3% | 1.20 | 2.56 |
| G59035cx | P | 3.09 | 2.58 | 0.25 | 7.61 | 5.73 | 1.89 | 24.8% | 1.20 | 1.78 |
| G59035lad | DES | 3.07 | 2.37 | 0.38 | 7.54 | 4.33 | 3.20 | 42.5% | 1.00 | 1.67 |
| G59036cx | P | 3.16 | 2.39 | 0.48 | 7.95 | 4.65 | 3.30 | 41.5% | 1.00 | 1.44 |
| G59036lad | P | 3.01 | 2.38 | 0.38 | 7.19 | 4.39 | 2.80 | 39.0% | 0.50 | 1.22 |
| G59037cx | P | 3.17 | 2.73 | 0.23 | 7.76 | 5.59 | 2.17 | 28.0% | 0.10 | 1.00 |
| G59037lad | P | 3.08 | 2.32 | 0.35 | 7.54 | 4.26 | 3.28 | 43.5% | 0.70 | 1.11 |
| G59038cx | P | | | | | | | | | |
| G59038lad | DEB | | | | | | | | | |
| G59039cx | DES | 2.89 | 2.05 | 0.48 | 6.55 | 3.26 | 3.28 | 50.2% | 1.90 | 1.00 |
| G59039lad | P | 3.13 | 2.10 | 0.61 | 7.80 | 3.43 | 4.36 | 56.0% | 1.30 | 2.00 |
| G59040cx | P | 3.03 | 2.18 | 0.32 | 7.25 | 3.74 | 3.51 | 48.4% | 1.70 | 1.22 |
| G59040lad | DES | 3.12 | 2.61 | 0.17 | 7.66 | 5.23 | 2.43 | 31.7% | 0.50 | 0.33 |
| G59041cx | DES | 2.84 | 2.26 | 0.22 | 6.49 | 4.05 | 2.45 | 37.7% | 0.70 | 1.22 |
| G59041lad | P | 3.27 | 2.05 | 0.61 | 8.38 | 3.59 | 4.79 | 57.1% | 1.70 | 2.33 |
| G59042cx | P | 2.84 | 2.29 | 0.25 | 6.23 | 3.96 | 2.27 | 36.4% | 0.90 | 4.00 |
| G59042lad | DEB | 3.14 | 2.29 | 1.88 | 5.47 | 5.18 | 0.29 | 5.2% | 0.80 | 0.33 |
| G59043cx | DES | 2.42 | 2.16 | 0.27 | 6.02 | 3.74 | 2.28 | 37.9% | 1.20 | 1.44 |
| G59043lad | P | 3.00 | 2.03 | 0.41 | 7.12 | 3.48 | 3.65 | 51.2% | 1.00 | 1.78 |
| G59044cx | P | 3.04 | 1.65 | 0.80 | 7.68 | 2.12 | 5.55 | 72.3% | 3.00 | 3.00 |
| G59044lad | DES | 2.96 | 2.00 | 0.44 | 7.02 | 3.31 | 3.71 | 52.9% | 3.00 | 3.00 |
| G59045cx | DES | 2.96 | 2.24 | 0.35 | 6.97 | 3.82 | 3.15 | 45.2% | 1.80 | 1.56 |
| G59045lad | P | 3.01 | 1.97 | 0.55 | 7.34 | 3.12 | 4.22 | 57.5% | 1.50 | 1.56 |
| G59046cx | DES | 2.91 | 1.98 | 0.44 | 7.09 | 3.36 | 3.73 | 52.6% | 1.90 | 2.44 |
| G59046lad | P | 2.96 | 1.50 | 1.00 | 7.09 | 1.83 | 5.27 | 74.2% | 1.90 | 1.44 |
| G59047cx | P | 2.98 | 2.21 | 0.36 | 7.21 | 3.78 | 3.43 | 47.5% | 2.00 | 1.78 |
| G59047lad | P | 2.98 | 1.56 | 0.79 | 7.20 | 1.90 | 5.30 | 73.6% | 1.80 | 1.22 |
| G59048cx | P | 3.10 | 2.63 | 0.14 | 7.61 | 5.15 | 2.46 | 32.3% | 0.60 | 1.00 |
| G59048lad | DES | 2.96 | 2.01 | 0.50 | 7.08 | 3.21 | 3.87 | 54.7% | 0.80 | 1.22 |
| G59049cx | P | 3.15 | 1.75 | 0.83 | 7.99 | 2.45 | 5.54 | 69.3% | 1.60 | 2.00 |
| G59049lad | DEB | 2.87 | 1.90 | 0.44 | 6.46 | 2.80 | 3.66 | 56.7% | 2.30 | 2.78 |
| G59050cx | P | 3.11 | 1.99 | 0.58 | 7.46 | 2.94 | 4.51 | 50.5% | 1.70 | 2.22 |
| G59050lad | P | 3.35 | 1.41 | 1.12 | 8.45 | 1.63 | 6.82 | 80.7% | 2.90 | 2.44 |

4. Conclusion:

The studies indicate show a significant reduction of neointimal formation by the Zotarolimus coated stent and coated balloon. The efficacy in reduction of neointimal formation by the Zotarolimus coated balloon is comparable to the Zotarolimus coated stent, and in some instances the zotarolimus coated balloon has greater efficacy than the zotarolimus coated stent.

As will be recognized by those of ordinary skill, the examples can be adapted to address situations for which it is desired to deliver multiple stents, e.g., "kissing" stents or overlapping stents.

What is claimed is:

1. A method for treating vascular disease comprising: providing a balloon having an outer surface and a coming disposed on at least a portion of the outer surface, the coating including an initial amount of a cytostatic agent selected from the group consisting of zotarolimus, everolimus, pimecrolimus, or a combination thereof, the coating being capable of maintaining a therapeutically effective amount of the cytostatic agent on the outer surface for delivery to a vessel wall; positioning the balloon at a lesion site along the vessel wall; and expanding the balloon for temporary contact of the outer surface with the vessel wall to deliver the therapeutically effective amount of the cytostatic agent to the vessel wall at the lesion site, wherein between about 4.9% to about 23% of the initial amount of the cytostatic agent remains disposed on the outer surface after delivery of the therapeutically effective amount of the cytostatic agent to the vessel wall.

2. The method of claim 1, wherein the cytostatic agent is zotarolimus.

3. The method of claim 2, wherein the zotarolimus is disposed on the outer surface at a concentration of between about 3.7 μg/mm$^2$ to about 7.0 μg/mm$^2$.

4. The method of claim 1, wherein the coating further comprises binders, polymers, solvents, or combinations thereof.

5. The method of claim 2, wherein the coating further comprises ethanol, Iopromide and acetone.

6. The method of claim 1, further comprising deploying a prosthesis at the lesion site.

7. The method of claim 6, wherein the prosthesis is a stent.

8. The method of claim 7 wherein the cytostatic agent is zotarolimus, and the therapeutically effective amount of zotarolimus is effective to maintain at least about 35.7% of a vessel lumen diameter after delivery of the therapeutically effective amount of zotarolimus.

9. The method of claim 7, wherein the stent is crimped onto the expandable member, the stent being deployed by expansion of the expandable member.

10. The method of claim 7, wherein the stent is a self-expanding stent.

11. The method of claim 4, wherein the binder is selected from the group consisting of complex sugars, starches, collagens, and polymeric materials.

12. The method of claim 1, wherein the coating includes a second beneficial agent.

13. The method of claim 1, wherein the therapeutically effective amount of the cytostatic agent is effective to reduce neointimal formation after delivery of the cytostatic agent to the vessel wall.

14. The method of claim 1, wherein the therapeutically effective amount of zotarolimus is delivered within about 60 seconds of contact between the expandable member in an expanded condition and the vessel wall.

* * * * *

UNITED STATES PATENT AND TRADEMARK OFFICE
CERTIFICATE OF CORRECTION

| | | |
|---|---|---|
| PATENT NO. | : 8,501,213 B2 | Page 1 of 1 |
| APPLICATION NO. | : 13/617628 | |
| DATED | : August 6, 2013 | |
| INVENTOR(S) | : John L. Toner et al. | |

It is certified that error appears in the above-identified patent and that said Letters Patent is hereby corrected as shown below:

IN THE CLAIMS:

At column 33, line 65:

"positioning the balloon at a lesion site along the vessel wail" should read

-- positioning the balloon at a lesion site along the vessel wall --

Signed and Sealed this
Twenty-second Day of October, 2013

Teresa Stanek Rea
*Deputy Director of the United States Patent and Trademark Office*